(12) United States Patent
Kozel et al.

(10) Patent No.: US 9,310,365 B2
(45) Date of Patent: Apr. 12, 2016

(54) METHOD OF DIAGNOSING AND TREATING MELIOIDOSIS

(75) Inventors: Thomas Kozel, Reno, NV (US); David Aucoin, Reno, NC (US)

(73) Assignee: The Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 87 days.

(21) Appl. No.: 13/639,450

(22) PCT Filed: Apr. 12, 2011

(86) PCT No.: PCT/US2011/032155
§ 371 (c)(1),
(2), (4) Date: Oct. 4, 2012

(87) PCT Pub. No.: WO2011/130301
PCT Pub. Date: Oct. 20, 2011

(65) Prior Publication Data
US 2013/0028927 A1     Jan. 31, 2013

Related U.S. Application Data

(60) Provisional application No. 61/323,236, filed on Apr. 12, 2010, provisional application No. 61/452,388, filed on Mar. 14, 2011.

(51) Int. Cl.
    *G01N 33/569*        (2006.01)
    *C07K 16/12*         (2006.01)

(52) U.S. Cl.
    CPC ...... *G01N 33/56911* (2013.01); *C07K 16/1214* (2013.01); *G01N 2333/21* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,451,507 A * | 9/1995 | Skold et al. | 435/7.92 |
| 2009/0191208 A1* | 7/2009 | Salzman et al. | 424/139.1 |

FOREIGN PATENT DOCUMENTS

| | | | |
|---|---|---|---|
| WO | WO 2008/017826 | * | 2/2008 |
| WO | WO 2008/017826 A2 | * | 2/2008 |
| WO | WO 2009/033013 | * | 3/2009 |
| WO | PCT/US2011/032155 | | 10/2011 |

OTHER PUBLICATIONS

Druar et al. Fems Immunology and Medical Microbiology, 52(2008): 78-87 published online Nov. 11, 2007.*
Rugdech et al. Am J. Trop. Med. Hyg, 1995, pp. 231-235.*
Anuntagool et al. Journal of Clinical Microbiology, Apr. 1996, p. 975-976, vol. 34, pp. 975-996.*
Leelarasamee. Curr Opinion Infect Dis 17:131-136, 2004.*
Druar et al. Fems Immunology and Medical Microbiology, 52 (2008):78-87 published online Nov. 11, 2007.*
Rugdech et al. Am J Trop Med Hyg, 1995, pp. 231-235.*
Anuntagool et al. Journal of Clinical Microbiology, Apr. 1996, vol. 34, p. 975-976.*
Declaration of Non-Establishment of International Search Report and Written Opinion, issued by the Korean Intellectual Property Office on Dec. 29, 2011, for corresponding PCT Patent Application No. PCT/US2011/032155, 4 pp.
Anuntagool, N., et al., Lipopolysaccharide from Nonvirulent Ara+ *Burkholderia pseudomallei* Isolates is Immunologically Indistinguishable from Lipopolysaccharide from Virulent Ara⁻ Clinical Isolates, Clin. Diagn. Lab. Immunol., Mar. 1998, 5(2):225-229.
Anuntagool, N., et al., Shedding of lipopolysaccharide and 200-kDa surface antigen during the in vitro growth of virulent Ara⁻ and avirulent Ara⁺*Burkholderia pseudomallei*, Acta Tropica, 2000, 74:221-228.
Brett, P., et al., Structural and immunological characterization of Burkholderia pseudomallei O-polysaccharide-flagellin protein conjugates, Infection and Immunity, Jul. 1996, 64(7):2824-2828.
Bryan, L., et al., Passive protection of diabetic rats with antisera specific for the polysaccharide portion of the lipopolysaccharide isolated from *Pseudomonas pseudomallei*, Can. J. Infect. Dis., 1994, 5(4):170-178.
Desakorn, V., et al., Detection of *Pseudomonas pseudomallei* Antigen in Urine for the Diagnosis of Melioidosis, Am. J. Trop. Med. Hyg., 1994, 51(5):627-633.
DeShazer, D., et al., Identification of a *Burkolderia mallei* polysaccharide gene cluster by subtractive hybridization and demonstration that the encoded capsule is an essential virulence determinant, Microbial Pathogenesis, 2001, 30:253-269.
Ho, M., et al., Specificity and Functional Activity of Anti-*Burkholderia pseudomallei* Polysaccharide Antibodies, Infection and Immunity, Sep. 1997, 65(9):3648-3653.
Jones, S.M., et al., Passive protection against *Burkholderia pseudomallei* infection in mice by monoclonal antibodies against capsular polysaccharide, lipopolysaccharide or proteins, J. Med. Microbiol., 2002, 51:1055-1062.

(Continued)

Primary Examiner — Oluwatosin Ogunbiyi
(74) Attorney, Agent, or Firm — Klarquist Sparkman, LLP

(57) ABSTRACT

Non-invasive methods are provided herein for the diagnosis of melioidosis with specific antibodies capable of detecting molecules associated with melioidosis in a biological fluid, such as urine or serum. These molecules can be identified using proteomic methods, including but not limited to antibody based methods, such as an enzyme-linked immunosorbant assay (ELISA), a radioimmunoassay (RIA), or a lateral flow immunoassay. Methods of inducing an immune response to melioidosis are also disclosed. The methods include the use of the immunogenic melioidosis polypeptides, nucleic acids encoding these polypeptides, and/or viral vectors encoding an immunogenic melioidosis polypeptide, alone or in conjunction with other agents, such as traditional melioidosis therapies. Also disclosed are methods for treating a subject having melioidosis. These methods include inducing an immune response to melioidosis and/or using an inhibitory nucleic acid, such as a siRNA or antisense molecule, to decrease a melioidosis associated molecule expression in order to treat melioidosis.

16 Claims, 18 Drawing Sheets

(56) References Cited

OTHER PUBLICATIONS

Nelson, M., et al., Evaluation of lipopolysaccharide and capsular polysaccharide as subunit vaccines against experimental melioidosis, J. Med. Microbiol., 2004, 53:1177-1182.

Nuti, D., et al., Identification of Circulating Bacterial Antigens by in Vivo Microbial Antigen Discovery, mBio, 2011, 2(4):1-11.

Reckseidler, S., et al., Detection of Bacterial Virulence Genes by Subtractive Hybridization: Identification of Capsular Polysaccharide of *Burkholderia pseudomallei* as a Major Virulence Determinant, Infection and Immunity, 2001, 69(1):34-44.

Reckseidler-Zenteno, S., et al., The Capsular Polysaccharide of *Burkholderia pseudomallei* Contributes to Survival in Serum by Reducing Complement Factor C3b Deposition, Infection and Immunity, 2005, 73(2):1106-1115.

Reckseidler-Zenteno, S., et al., Genetics and Function of the Capsules of *Burkholderia pseudomallei* and their Potential as Therapeutic Targets, Mini-Reviews in Medicinal Chemistry, 2009, 9:265-271.

Steinmetz, I., et al., Purification and Characterization of an Exopolysaccharide of (*Pseudomonas*) *pseudomallei*, Infection and Immunity, 1995, 63(10):3959-3965.

Wiersinga, W. J., et al., Melioidosis, New England J. Med., 2012, 367:1035-1044.

Wuthiekanun, V., et al., Short Report: Quantitation of *B. pseudomallei* in Clinical Samples, Am. J. Trop. Med. Hyg., 2007, 77(5):812-813.

* cited by examiner

FIG. 3

FIG. 4
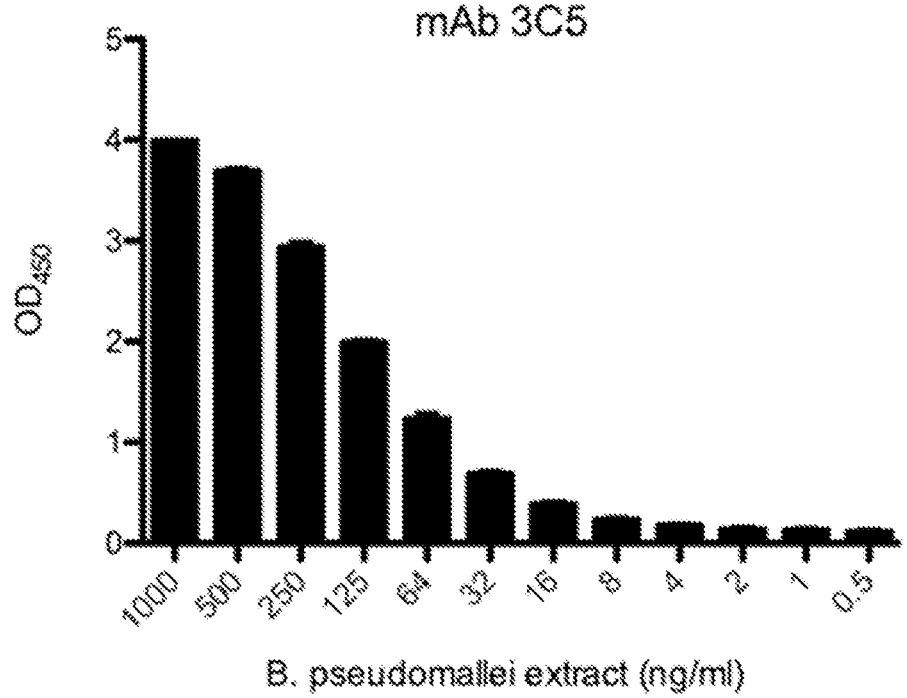
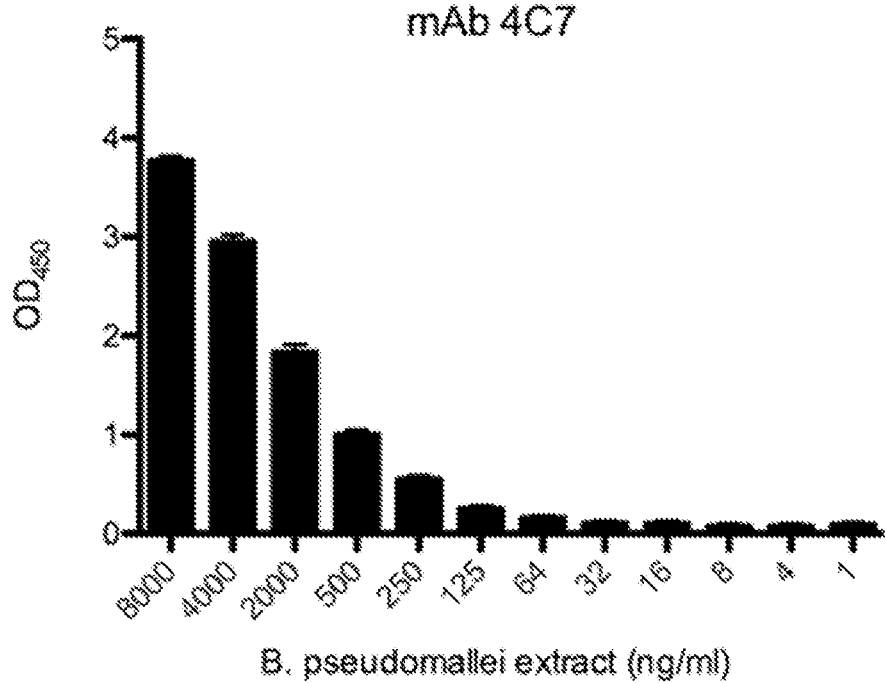

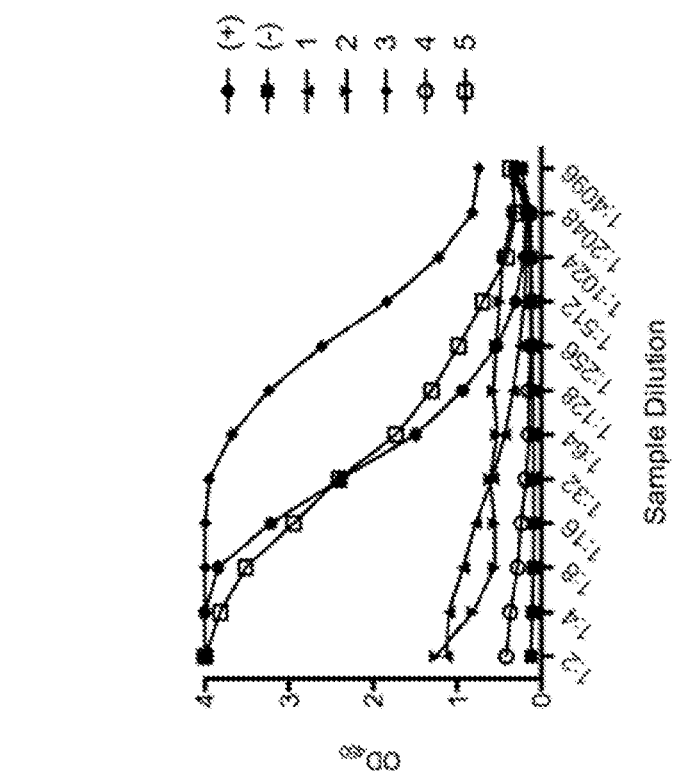
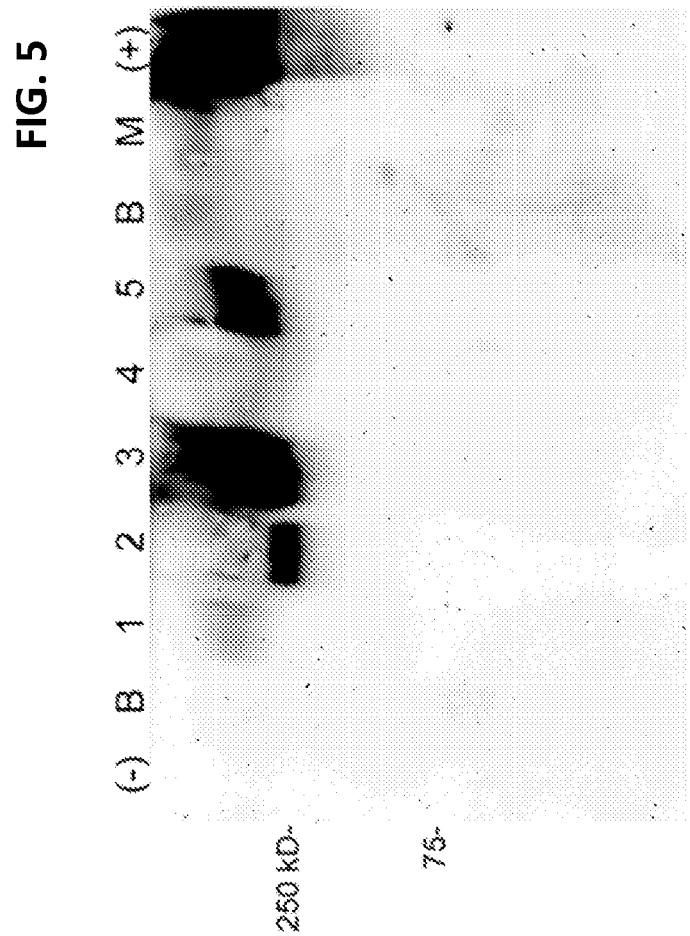
FIG. 5

Passive protection with CPS and LPS mAbs

FIG. 6B
**CPS mAb latex agglutination of *Bp* whole cells**

| | | | |
|---|---|---|---|
| $1.3 \times 10^8$ | $6.5 \times 10^7$ | $3.3 \times 10^7$ | $1.6 \times 10^7$ |
| $8.3 \times 10^6$ | $4.2 \times 10^6$ | $2.1 \times 10^6$ | PBS |

Cells/20ul

FIG. 7

Lateral flow immunoassay for detection of CPS and LPS

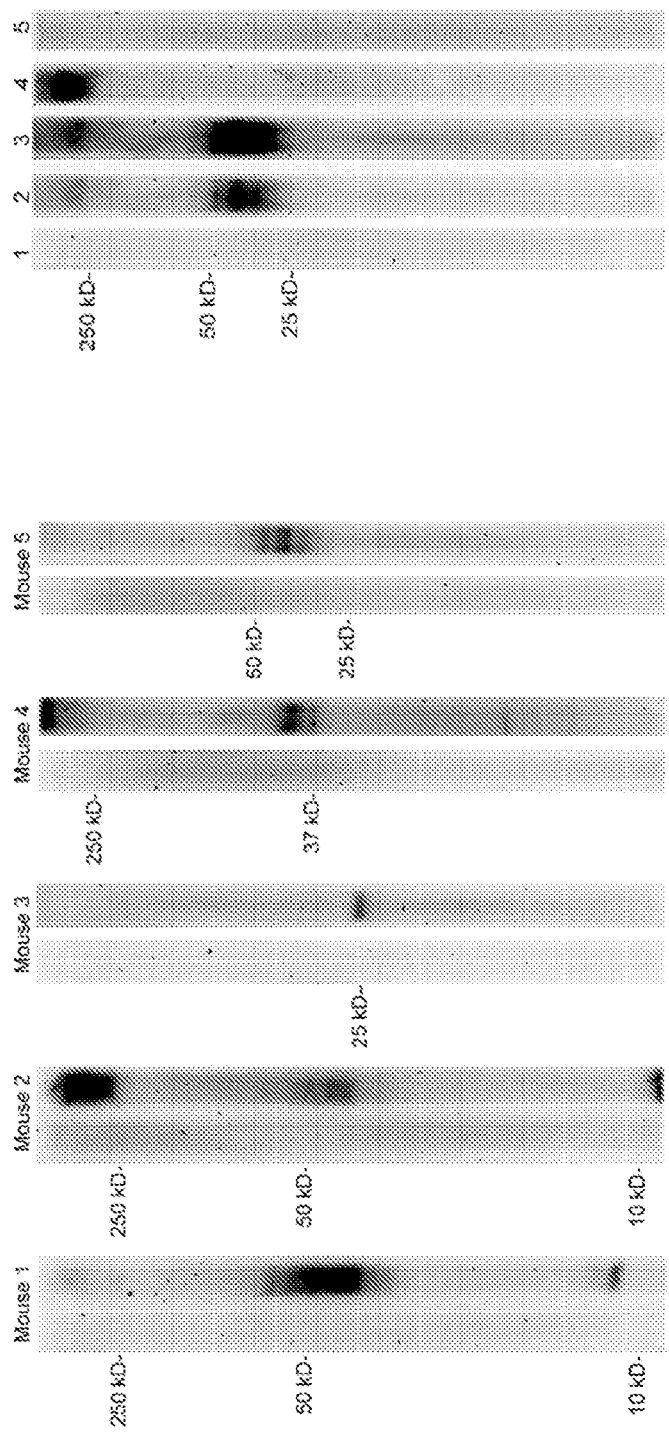

FIG. 11

*B. pseudomallei*-specific CPS and LPS mAbs

Detection of CPS in melioidosis patient urine

Detection of flagellin in melioidosis patient urine

Detection of GroEL in melioidosis patient urine

```
SEQUENCE LISTING

<160> NUMBER OF SEQ ID NOS: 1

<210> SEQ ID NO 1
<211> LENGTH: 14
<212> TYPE: PRT
```

```
<213> ORGANISM: Agrobacterium H13-3

<400> SEQUENCE: 1

Thr Glu Val Glu Val Lys Glu Lys Lys Asp Arg Val Asp Asp
1               5                   10
```

METHOD OF DIAGNOSING AND TREATING MELIOIDOSIS

CROSS REFERENCE TO RELATED APPLICATIONS

This is the U.S. National Stage of International Application No. PCT/US2011/032155, filed Apr. 12, 2011, which was published in English under PCT Article 21(2), which in turn claims the benefit of U.S. Provisional Application No. 61/323,236, filed on Apr. 12, 2010 and U.S. Provisional Application No. 61/452,388, filed on Mar. 14, 2011, each of which is incorporated herein by reference in its entirety.

ACKNOWLEDGMENT OF GOVERNMENT SUPPORT

This invention was made with government support under Grant No. AI065359 awarded by the National Institutes of Health. The government has certain rights in the invention.

FIELD

This relates to the field of melioidosis, specifically to the identification of subjects who have melioidosis, monitoring the effectiveness of treatments for melioidosis and treating melioidosis.

BACKGROUND

Melioidosis is an infectious disease caused by a Gram-negative bacterium, *Burkholderia pseudomallei*, found in soil and water. Melioidosis is endemic in parts of the world including Southeast Asia (including Thailand, Singapore, Malaysia, Burma and Vietnam), Taiwan and northern Australia. Multiple cases have also been described in southern China and Hong Kong, Brunei, India, and Laos, and sporadic cases in Central and South America, the Middle East, the Pacific and several African countries. Estimates of the global infections are most likely underestimated due to the lack of proper microbiological laboratories. In northeast Thailand, *B. pseudomallei* is the cause of 20% of all community-acquired septicemias with a mortality rate of 50%. The bacterium is also responsible for 40% of all mortality due to sepsis in this same geographical region. In regions of northern Australia, where intensive care treatment is more readily available, the mortality rate is still unacceptably high at 20%. Moreover, relapse rates can be as high as 25%.

SUMMARY

Development of effective therapeutics and diagnostics for melioidosis is of importance to reduce mortality in endemic regions and provide protection in bioterrorism-targeted areas. Currently, culture from multiple body sites is the gold standard for laboratory diagnosis of melioidosis. However, culture requires experienced personnel and takes 3-4 days. A high percentage of patients with acute septicemia die within 24-48 hours of admission, and the antibiotics used for empiric treatment of septicemia are not effective for *B. pseudomallei*. Assays for antibody have previously been shown to be of limited value due to an absence of antibody in the early stages of acute sepsis and a high level of background antibodies in endemic regions. Further, levels of bacteremia are very low (~1 CFU/ml) and difficult to detect. For example, several studies reported PCR for detection of *B. pseudomallei*, but the reported lower limit of detection tends to fall above the range for the viable bacteria count in blood during human disease.

A point-of-care immunoassay for diagnosis of melioidosis including agents capable of detecting low levels of bacteremia could greatly impact patient outcome because they would be able to detect the bacteria within minutes or hours from testing as compared to days required with the current methods. Earlier detection translates into earlier administration of therapies which could significantly increase the likelihood of patient survival as well as decrease the severity of the disease.

Lipopolysaccharide (LPS), exopolysaccharide (EPS) and capsular polysaccharide (CPS) are virulence factors produced by *B. pseudomallei*. LPS is an unbranched polymer of disaccharide repeating units having the basic structure: [-3-)-β-D-glucopyranose-(1-3)-6-deoxy-α-L-talopyranose-(1-]. EPS is an unbranched polymer of a repeating tetrasaccharide: [-3)-β-D-Galp2Ac-(1-4)-α-D-Galp-(1-3)-β-D-Galp-(1-5)-β-Kdo-(2-]. CPS is an unbranched homopolymer of 6-deoxy-D-manno-heptose. Here the inventors have produced monoclonal antibodies (mAbs), mAb 4C7 and mAb 3C5, specific to the LPS and the CPS of *B. pseudomallei*. Both mAbs are reactive with proteinase-K insensitive *B. pseudomallei* antigens by Western blot. Passive immunization studies in a pulmonary model of melioidosis determined that both mAbs offer protection. For example, the CPS mAb had the ability to detect antigen in urine samples from melioidosis patients by antigen-capture ELISA and Western blot. The inventors have also produced a monoclonal antibody specific to EPS of *B. pseudomallei*. Further, the inventors have identified protein antigens that are detected in subjects with melioidosis (see Table 2). In particular, GroEl and flagellin were observed to be present in urine samples obtained from patients with melioidosis.

Based upon these findings, compositions and methods of using such for diagnosing, monitoring and treating melioidosis are disclosed. In particular, monoclonal antibodies (mAbs) specific for LPS, CPS and/or EPS of *B. pseudomallei* are disclosed. Methods for diagnosing and/or monitoring acute and chronic melioidosis are provided. Methods for treating a subject with melioidosis or at risk of acquiring it are also disclosed which include administering therapeutically effective concentrations of one or more of the disclosed monoclonal antibodies to protect the subject from melioidosis or inhibit one or more sign or symptoms associated with melioidosis. Also disclosed are immunoassays that can be used to diagnosis or monitor the efficacy of melioidosis treatment. These immunoassays can also be used for rapid diagnosis of infection produced by Category A and B bio-threats as defined by the United States Government, in addition to *B. pseudomallei* or other melioidosis associated molecules.

In one particular embodiment, a method of diagnosing a subject with melioidosis or monitoring the efficacy of a therapy comprises detecting at least one melioidosis-associated molecule in a sample obtained from a subject exhibiting one or more signs or symptoms associated with melioidosis or a subject known to be at risk of acquiring melioidosis, thereby diagnosing the subject. In one example, the at least one melioidosis-associated molecule is at least one antigen listed in Table 2, such as GroEL. In some examples, the at least one melioidosis-associated molecule comprises detecting at least one antigen listed in Table 2 and at least one of LPS, CPS, BipC, flagellin or a combination thereof. In one example, the at least one antigen listed in Table 2 is GroEL. In one example, detecting at least one melioidosis-associated molecule includes detecting at least GroEL, BipC and flagellin.

In some examples, the method further comprises comparing detection of the at least one melioidosis-associated molecule in the sample obtained from the subject exhibiting one or more signs or symptoms associated with melioidosis to a control, wherein increased detection of the at least one melioidosis-associated molecule relative to a control indicates that the subject has melioidosis.

In one example, detecting of that at least one melioidosis-associated molecule comprises usage of at least one antibody specific for the at least one melioidosis-associated molecule, such as an antibody specific for GroEL or one or more mAbs specific for B. pseudomallei LPS, EPS or CPS. For example, the monoclonal antibody is mAb 3C5 or mAb 4C7.

In some examples, the method is used for detecting any condition or disease associated with B. mallei, B. pseudomallei, B. thailandensis or a combination thereof. In some examples, the disclosed method is used for diagnosing a subject with acute melioidosis. In some examples, the method is used for diagnosing a subject with chronic melioidosis. In some examples, the method is a method for monitoring the efficacy of therapy.

In one example, detecting at least one melioidosis-associated molecule comprises using a lateral flow device.

In some examples, the sample is a urine or serum sample.

In some embodiments, the method further comprises comparing detection of the at least one melioidosis-associated molecule in the sample obtained from the subject exhibiting one or more signs or symptoms associated with melioidosis to a control, wherein increased detection of the at least one melioidosis-associated molecule relative to a control indicates that the subject has melioidosis. In some examples, the method is used for diagnosing a subject with acute melioidosis. In some examples, the method is used for diagnosing a subject with chronic melioidosis. In one example, the method is a method for monitoring the efficacy of therapy. In some examples, detecting at least one melioidosis-associated molecule comprises using a lateral flow device. In some examples, the method is used for detecting any condition or disease associated with B. mallei, B. pseudomallei, B. thailandensis or a combination thereof.

Methods of inducing an immune response to melioidosis are also disclosed. The methods include the use of the immunogenic melioidosis polypeptides, nucleic acids encoding these polypeptides, and/or viral vectors encoding an immunogenic melioidosis polypeptide, alone or in conjunction with other agents, such as traditional melioidosis therapies. Also disclosed are methods for treating a subject having melioidosis. These methods include inducing an immune response to melioidosis and/or using an inhibitory nucleic acid, such as a siRNA or antisense molecule, to decrease a melioidosis associated molecule expression in order to treat melioidosis.

The foregoing and other features will become more apparent from the following detailed description of several embodiments, which proceeds with reference to the accompanying figures.

BRIEF DESCRIPTION OF THE FIGURES

FIG. 10 is a digital image of a Western blot analysis illustrating reactive proteins identified by InMAD.

Figure 11:
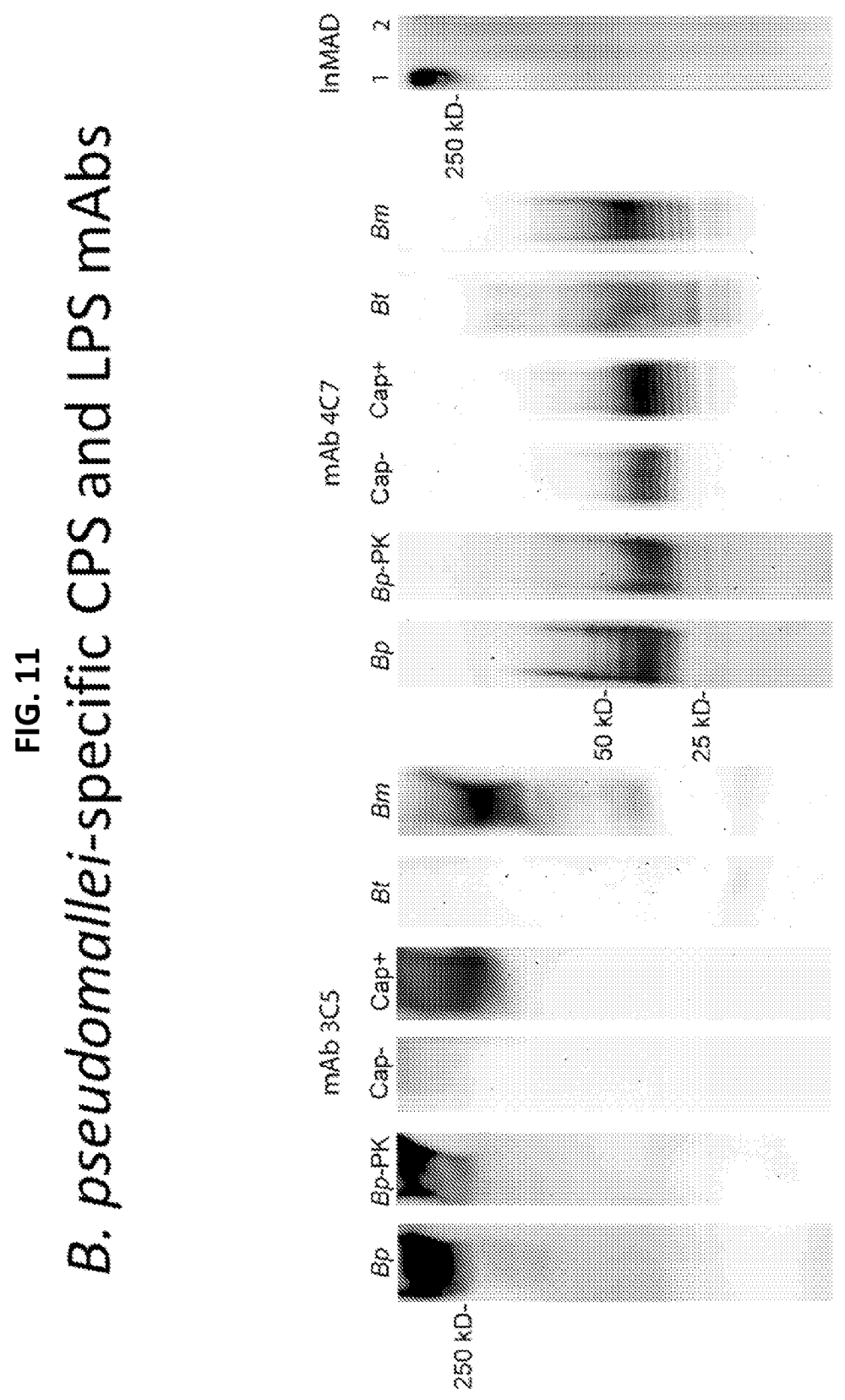

FIG. 11 is a digital image of a Western blot analysis illustrating detection of polysaccharide antigens LPS and CPS.

DETAILED DESCRIPTION OF SEVERAL EMBODIMENTS

I. Terms

Figure 1:
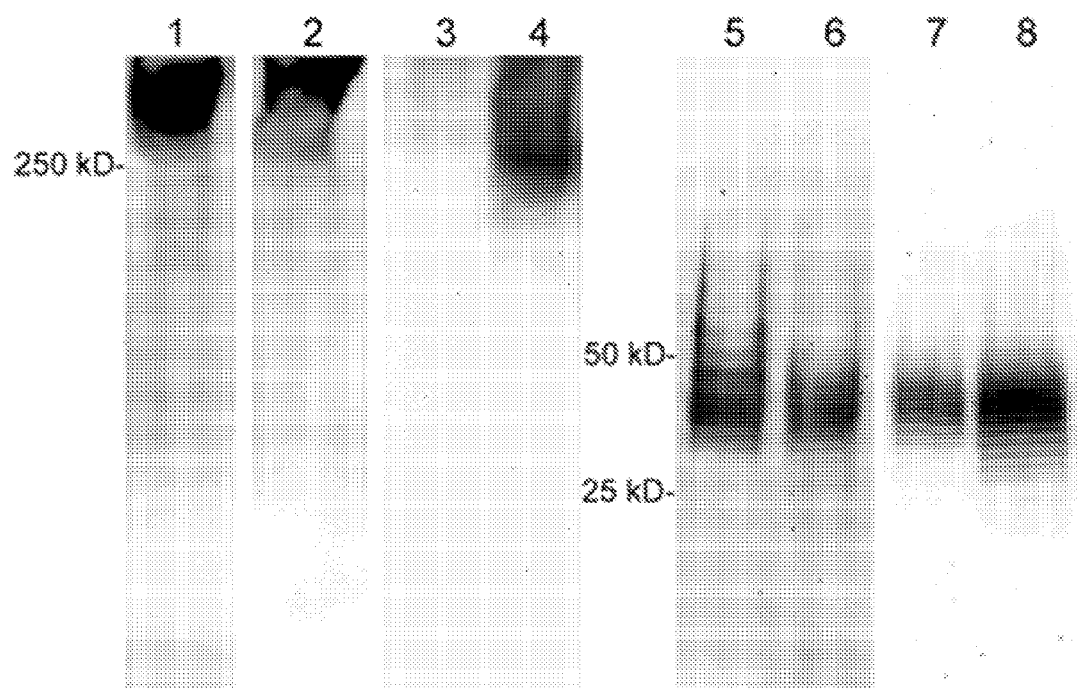
FIG. 1 is a Western blot analysis probing with B. pseudomallei specific mAbs. mAb 3C5 (lanes 1-4)
Figure 2:
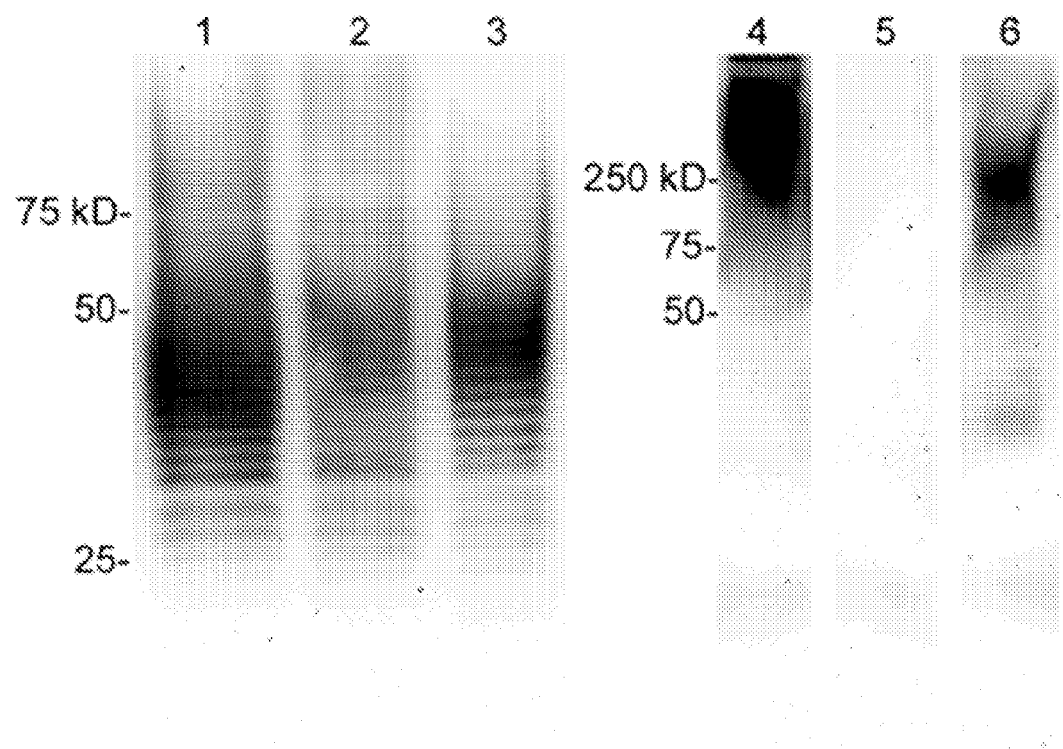
Figure 6A:
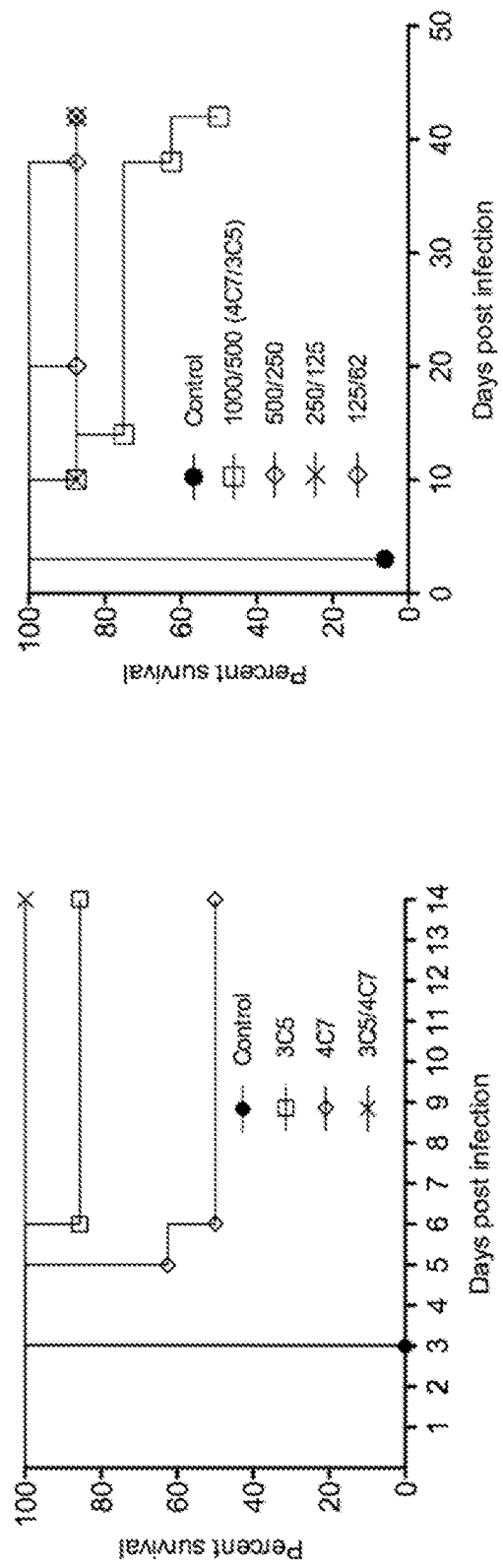

Unless otherwise explained, all technical and scientific terms used herein have the same meaning as commonly understood by one of ordinary skill in the art to which this disclosure belongs. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN1-56081-569-8).

The singular terms “a,” “an,” and “the” include plural referents unless context clearly indicates otherwise. Similarly, the word “or” is intended to include “and” unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term “comprises” means “includes.” All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of this disclosure, the following explanations of specific terms are provided:

Adjuvant: A vehicle used to enhance antigenicity. Adjuvants include a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunstimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). Adjuvants include biological molecules (a “biological adjuvant”), such as costimulatory molecules. Exemplary adjuvants include IL-2, RANTES, GM-CSF, TNF-α, IFN-γ, G-CSF, LFA-3, CD72, B7-1, B7-2, OX-40L and 41 BBL.

Animal: Living multi-cellular vertebrate organisms, a category that includes, for example, mammals and birds. The term mammal includes both human and non-human mammals. Similarly, the term “subject” includes both human and veterinary subjects, for example mice.

Antibody: A polypeptide ligand comprising at least a light chain or heavy chain immunoglobulin variable region which specifically binds an epitope of a protein listed in the tables below, or a fragment of any of these proteins. Antibodies can include a heavy chain and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins (“scFv”), and disulfide stabilized Fv proteins (“dsFv”). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes recombinant forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A “monoclonal antibody” is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. These fused cells and their progeny are termed “hybridomas.” Monoclonal antibodies include humanized monoclonal antibodies.

A variety of immunoassay formats are appropriate for selecting antibodies specifically immunoreactive with a particular protein. For example, solid-phase ELISA immunoassays are routinely used to select monoclonal antibodies specifically immunoreactive with a protein. See Harlow & Lane, Antibodies, *A Laboratory Manual*, Cold Spring Harbor Publications, New York (1988), for a description of immunoassay formats and conditions that can be used to determine specific immunoreactivity.

Binding: A specific interaction between two or more molecules, such as the binding of an antibody and an antigen (for example an antibody to an antigen). In one embodiment, specific binding is identified by a dissociation constant ($K_d$). In one embodiment, binding affinity is calculated by a modification of the Scatchard method described by Frankel et al., *Mol. Immunol.,* 16:101-106, 1979. In another embodiment, binding affinity is measured by an antigen/antibody dissociation rate. In yet another embodiment, a high binding affinity is measured by a competition radioimmunoassay (RIA). In several examples, a high binding affinity is at least about $1\times10^{-8}$ M. In other embodiments, a high binding affinity is at least about $1.5\times10^{-8}$, at least about $2.0\times10^{-8}$, at least about $2.5\times10^{-8}$, at least about $3.0\times10^{-8}$, at least about $3.5\times10^{-8}$, at least about $4.0\times10^{-8}$, at least about $4.5\times10^{-8}$, or at least about 5.0×10⁻⁸ M. In one example, the disclosed antibodies have a binding affinity for the melioidosis associated antigen of at least 10 nM.

Contacting: "Contacting" includes in solution and solid phase, for example contacting a salivary protein with a test agent. The test agent may also be a combinatorial library for screening a plurality of compounds. In another example, contacting includes contacting a sample with an antibody, for example contacting a sample that contains a protein of interest such as a protein associated with melioidosis, such as LPS, CPS, flagellin, GroEL, or BipC.

CPS: An unbranched homopolymer of [-3)-2-O-acetyl-6-deoxy-β-D-manno-heptopyranose-(1-].

Effector protein BipC (BipC): A protein that belongs to the invasion protein C family. Human melioidoisis patients have detectable antibody response to BipC.

The term BipC includes any BipC gene, cDNA, mRNA, or protein from any organism. In one example, BipC is used to detect and diagnosis melioidosis.

Exemplary nucleic acid and protein sequences for BipC are publicly available (see, EMBL Accession Nos. EF428329, EF428332, EF436254, and BX571966 for exemplary genomic DNA sequences and EMBL Accession Nos. ABO26349.1, ABO26355.1, ABO28815.1, and CAH39004.1 for exemplary protein sequences (each of which hereby incorporated by reference as available on Mar. 14, 2011)). The 3-dimensional structure of BipC is also publically available (see, ProteinModelPortal Q63K35; which is hereby incorporated by reference as available on Mar. 14, 2011).

In one example, BipC includes a full-length wild-type (or native) sequence, as well as BipC allelic variants, fragments, homologs or fusion sequences that retain the ability to be detected in a subject with melioidosis. In certain examples, BipC has at least 80% sequence identity, for example at least 85%, 90%, 95%, or 98% sequence identity to a known BipC and retains BipC activity (e.g., the capability to be detected in a subject with melioidosis).

EPS: An unbranched polymer of a repeating tetrasaccharide: [-3)-β-D-Galp2Ac-(1-4)-α-D-Galp-(1-3)-β-D-Galp-(1-5)-β-Kdo-(2-].

Flagellin: A protein that arranges itself in a hollow cylinder to form the filament in bacterial flagellum. It has a mass of about 30,000 to 60,000 daltons. Flagellin is the principal substituent of bacterial flagellum, and is present in large amounts on nearly all flagellated bacteria. In one example, flagellin is used as a marker of meliodosis.

GroEL: A protein that belongs to the alkalai family of molecular chaperones, and is found in a large number of bacteria. It is known to play a role in protein folding. To function properly, GroEL requires the lid-like co-chaperonin protein complex GroES. In eukaryotes, the protein Hsp60 is believed to be structurally and functionally nearly identical to GroEL.

Exemplary nucleic acid and protein sequences for GroEL are publicly available (see, GenBank Nos. NM_002156 (human) and NM_010477 (mouse) for GroEL nucleic acid sequences and NP_002147 (human) and NP_034607 (mouse) for GroEL protein sequences; each of which hereby incorporated by reference as available on Mar. 14, 2011).

In one example, GroEL includes a full-length wild-type (or native) sequence, as well as GroEL allelic variants, fragments, homologs or fusion sequences that retain the ability to be detected in a subject with melioidosis. In certain examples, GroEL has at least 80% sequence identity, for example at least 85%, 90%, 95%, or 98% sequence identity to a known GroEL and retains GroEL activity (e.g., the capability to be detected in a subject with melioidosis).

In one example, a GroEL peptide is used for immunization. For example, a GroEL peptide with an amino acid sequence of C-TEVEVKEKKDRVDD (SEQ ID NO:1; starting at residue 385 of *Agrobacterium* sp. H13-3 GenBank Accession No. YP_004280298; which is hereby incorporated by reference as available on Mar. 14, 2011) is used for immunization.

Immunoassay: A biochemical test that measures the presence or concentration of a substance in a sample, such as a biological sample, using the reaction of an antibody to its cognate antigen, for example the specific binding of an antibody to a protein. Both the presence of antigen or the amount of antigen present can be measured. For measuring proteins, for each the antigen and the presence and amount (abundance) of the protein can be determined or measured. Measuring the quantity of antigen can be achieved by a variety of methods. One of the most common is to label either the antigen or antibody with a detectable label.

A "competitive radioimmunoassay (RIA)" is a type of immunoassay used to test for antigens (for example, proteins present in a sample, such as a biological sample). In some examples it involves mixing known quantities of radioactive antigen (for example a radioactively labeled protein, such as a $^{125}$I labeled protein) with antibody to that antigen, then adding unlabeled or "cold" antigen (for example unlabeled antigen present in a sample, such as biological sample obtained from a subject, such as a biological fluid) and measuring the amount of labeled antigen displaced by the unlabeled antigen.

Initially, the radioactive antigen is bound to the antibodies. When "cold" (i.e. unlabeled) antigen is added, the two compete for antibody binding sites at higher concentrations of "cold" antigen, more of it binds to the antibody, displacing the radioactive variant. The bound antigens are isolated from the unbound ones and the amount of radioactivity measured. A radioimmunoassay can be used to calculate the amount of an antigen in a sample.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunogenic peptides can also be identified by measuring their binding to a specific MHC protein (e.g. HLA-A02.01) and by their ability to stimulate CD4 and/or CD8 when presented in the context of the MHC protein. The characteristics of immunogenic polypeptides, are disclosed, for example, in PCT Publication No. WO 00/12706, which is incorporated herein by reference.

In one example, an immunogenic "melioidosis peptide" is a series of contiguous amino acid residues from a melioidosis associated protein, such as an antigen provided in Table 2, generally between 7 and 20 amino acids in length, such as about 8 to 15 residues in length. In some examples, an immunogenic melioidosis peptide is a series of contiguous amino acid residues from BipC, flagellin or GroEL, generally between 7 and 20 amino acids in length, such as about 8 to 15 residues in length. For example, a GroEL immunogenic peptide is a peptide with an amino acid sequence of C-TEVEVKEKKDRVDD (SEQ ID NO:1; starting at residue 385 of *Agrobacterium* sp. H13-3 GenBank Accession No. YP_004280298; which is hereby incorporated by reference as available on Mar. 14, 2011).

Generally, immunogenic melioidosis polypeptides can be used to induce an immune response in a subject, such as a B cell response or a T cell response. In one example, an immunogenic melioidosis polypeptide, when bound to a Major Histocompatibility Complex Class I molecule, activates cytotoxic T lymphocytes (CTLs) against cells expressing wild-type melioidosis associated protein, such as one or more antigens listed in Table 2. Induction of CTLs using synthetic peptides and CTL cytotoxicity assays known in the art, see U.S. Pat. No. 5,662,907, which is incorporated herein by reference. In one example, an immunogenic peptide includes an allele-specific motif or other sequence such that the peptide will bind an MHC molecule and induce a cytotoxic T lymphocyte ("CTL") response against the antigen from which the immunogenic peptide is derived.

Immunogenic composition: A composition comprising an immunogenic melioidosis polypeptide or a nucleic acid encoding the immunogenic melioidosis-associated polypeptide that induces a measurable CTL response against cells expressing melioidosis polypeptide, or induces a measurable B cell response against a melioidosis-associated polypeptide. For in vitro use, the immunogenic composition can consist of the isolated nucleic acid, vector including the nucleic acid/or immunogenic peptide. For in vivo use, the immunogenic composition will typically comprise the nucleic acid, vector including the nucleic acid, and or immunogenic polypeptide, in pharmaceutically acceptable carriers, and/or other agents. An immunogenic composition can optionally include an adjuvant, a costimulatory molecule, or a nucleic acid encoding a costimulatory molecule. A melioidosis-associated polypeptide, or nucleic acid encoding the polypeptide, can be readily tested for its ability to induce a CTL by art-recognized assays.

Inhibiting or treating a disease: A phrase used to refer to inhibiting the full development of a disease, such as melioidosis. In several examples, inhibiting a disease refers to lessening symptoms of melioidosis. "Treatment" refers to a therapeutic intervention that ameliorates a sign or symptom of a disease or pathological condition related to the disease, such as melioidosis.

Label: A detectable compound or composition that is conjugated directly or indirectly to another molecule, such as an antibody or a protein, to facilitate detection of that molecule. Specific, non-limiting examples of labels include fluorescent tags, enzymatic linkages (such as horseradish peroxidase), radioactive isotopes (for example $^{14}C$, $^{32}P$, $^{125}I$, $^{3}H$ isotopes and the like) and particles such as colloidal gold. In some examples a protein, such as a protein associated with melioidosis, is labeled with a radioactive isotope, such as 14C, $^{32}P$, $^{125}I$, $^{3}H$ isotope. In some examples an antibody that specifically binds the protein is labeled. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998), Harlow & Lane (Antibodies, *A Laboratory Manual*, Cold Spring Harbor Publications, New York, 1988).

LPS: An unbranched polymer of disaccharide repeating units having the basic structure: [-3-)-β-D-glucopyranose-(1-3)-6-deoxy-α-L-talopyranose-(1-].

Lymphocytes: A type of white blood cell that is involved in the immune defenses of the body. There are two main types of lymphocytes: B cells and T cells.

Major Histocompatibility Complex (MHC): A generic designation meant to encompass the histocompatability antigen systems described in different species, including the human leukocyte antigens ("HLA").

Melioidosis: An infectious disease caused by a Gram-negative bacterium, *Burkholderia pseudomallei*, found in soil and water. It is of public health importance in endemic areas, particularly in Thailand and northern Australia. It exists in acute and chronic forms. Symptoms may include pain in chest, bones, or joints; cough; skin infections, lung nodules and pneumonia. *B. pseudomallei* was thought to be a member of the *Pseudomonas* genus and was previously known as *Pseudomonas pseudomallei*. It is phylogenetically related closely to *Burkholderia mallei* which causes glanders, an infection primarily of horses, donkeys and mules.

Acute melioidosis normally has an incubation period of less than a month. Patients with latent melioidosis may be symptom free for decades. Chronic melioidosis is usually defined by a duration of symptoms greater than 2 months and occurs in approximately 10% of patients. The clinical presentation of chronic melioidosis is protean and includes such presentations as chronic skin infection, skin ulcers and lung nodules or chronic pneumonia. A patient with active melioidosis may present a fever or other pain or other symptoms such as cough, pleuritic chest pain, bone or joint pain, or intra-abdominal infection (including liver and/or splenic abscesses, or prostatic abscesses)

A current treatment of melioidosis may be divided into two stages, an intravenous high intensity stage and an oral maintenance stage to prevent recurrence. The intravenous intensive phase may include the following. Intravenous ceftazidime for treatment of acute melioidosis. Meropenem, imipenem and cefoperazone-sulbactam (Sulperazone) are also active. Intravenous amoxicillin-clavulanate (co-amoxiclav) may also be used. Intravenous antibiotics are typically given for a minimum of 10 to 14 days, and are continued until the patient's temperature has returned to normal for more than 48 hours: it is not uncommon for patients to require parenteral treatment continuously for more than a month. Additional possible therapeutic agents include cefepime, ertapenem, piperacillin-sulbactam, doripenem and biapenem.

Following the treatment of the acute disease, a maintenance treatment may be provided to the patient such as administration of co-trimoxazole and doxycycline for a period of time (such as 12 to 20 weeks) to reduce the rate of recurrence. Other maintenance treatments may include administration of chloramphenicol and co-amoxiclav.

The methods, compositions and assays disclosed herein provide a means of identifying a subject who has melioidosis or who is at increased risk of developing melioidosis. A "non-melioidosis" or "normal" subject does not have any form of melioidosis.

A "melioidosis-associated molecule" is a molecule associated with one or more signs or symptoms of melioidosis. In some examples, a melioidosis-associated molecule is one or more of the antigens provided in Table 2. In some examples, a melioidosis-associated molecule is LPS, CPS, BipC, flagellin or GroEL.

Peptide Modifications: Melioidosis-associated peptides include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, can be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, can be in the form of a pharmaceutically-acceptable acid addition salt, such as the HCl, HBr, acetic, benzoic, toluene sulfonic, maleic, tartaric and other organic salts, or can be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of an immunogenic melioidosis polypeptide having measurable or enhanced ability to generate an immune response. For computer modeling applications, a pharmacophore is an idealized three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," in Klegerman & Groves, eds., 1993, *Pharmaceutical Biotechnology*, Interpharm Press: Buffalo Grove, Ill., pp. 165-174 and *Principles of Pharmacology*, Munson (ed.) 1995, Ch. 102, for descriptions of techniques used in CADD. Also included are mimetics prepared using such techniques.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition (1995), describes compositions and formulations suitable for pharmaceutical delivery of the melioidosis-associated peptides herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (e.g., glycosylation or phosphorylation). In one embodiment, the polypeptide is a melioidosis-associated polypeptide. A polypeptide can be between 3 and 30 amino acids in length. In one embodiment, a polypeptide is from about 7 to about 25 amino acids in length. In yet another embodiment, a polypeptide is from about 8 to about 15 amino acids in length. In yet another embodiment, a peptide is about 14 amino acids in length. With regard to polypeptides, the word "about" indicates integer amounts. Thus, in one example, a polypeptide "about" 9 amino acids in length is from 8 to 10 amino acids in length.

Therapeutic agent: A substance that demonstrates some therapeutic effect by restoring or maintaining health, such as by alleviating the symptoms associated with a disease or physiological disorder, or delaying (including preventing) progression or onset of a disease. In some instances, the therapeutic agent is a chemical or pharmaceutical agent, or a prodrug. A therapeutic agent may be an agent which prevents or inhibits one or more signs or symptoms or laboratory findings associated with melioidosis.

A "therapeutically effective amount" or "therapeutically effective dose" is that amount or dose sufficient to inhibit or prevent onset or advancement, to treat outward symptoms, or to cause regression, of a disease. The therapeutically effective amount or dose also can be considered as that amount or dose capable of relieving symptoms caused by the disease. Thus, a therapeutically effective amount or dose of an anti-melioidosis agent is that amount or dose sufficient to achieve a stated therapeutic effect.

II. Methods for Detecting Melioidosis and Monitoring the Efficacy of a Therapeutic Regimen Methods are disclosed herein that are of use to determine if a subject has melioidosis, including acute or chronic melioidosis, or to monitor the efficacy of therapy. These methods utilize a biological fluid, such as, but not limited to urine or serum, for the detection of a molecule associated with melioidosis, including, but not limited to, protein antigens listed in Table 2 (such as GroEL), flagellin, BipC, LPS, CPS, EPS or a combination thereof. The melioidosis molecules include any naturally occurring forms of the proteins, such as but not limited to glycosylated forms. In some embodiments, the methods disclosed herein are used to identify a subject as having acute melioidosis. In other embodiments, the methods are used to identify chronic melioidosis. In even further embodiments, the methods are used to diagnosis latent melioidosis. These methods can be performed over time, to monitor the progression or regression of melioidosis in a subject, or to assess for the development of melioidosis from a pre-melioidosis condition.

Methods are disclosed herein that include testing a biological sample, such as a serum or urine sample, obtained from the subject. In one example, the biological sample is a biological fluid, such as urine. However, other biological fluids are also of use, such as blood, GCF, amniotic fluid, salvia or tears. The methods include detecting, or determining the abundance (amount) of one or more molecules associated with melioidosis, including protein antigens listed in Table 2 (such as GroEL), flagellin, BipC, LPS, CPS, EPS or a combination thereof. In some examples, the methods include determining a proteomic profile.

In one example, the method includes detecting at least GroEL. In one example, the method includes detecting GroEL and at least one more molecule associated with melioidosis such as LPS, CPS and/or EPS of *B. pseudomallei*. In one example, the method includes detecting GroEL and flagellin. In one example, the method includes detecting GroEL, flagellin and BipC. The methods can include detecting at least one, such as two, three, four, five, six, seven, eight, nine, ten, eleven, twelve, thirteen, fourteen, fifteen, sixteen, seventeen, eighteen, nineteen, twenty, twenty-one or more molecules associated with melioidosis. In one example, the method includes detecting at least one, such as two, three, four, five, six, seven, eight, nine, ten, eleven, twelve, thirteen, fourteen, fifteen or sixteen molecules listed in Table 2.

In some embodiments, the method includes detecting an increase, such as a statistically significant increase, such as an at least a 1.5, 2, 3, 4, or 5 fold increase in the amount of one or more molecules associated with melioidosis, including at least a 1.5, 2, 3, 4, or 5 fold increase in one or more protein antigens listed in Table 2, flagellin, BipC, LPS, CPS and/or EPS of *B. pseudomallei* as compared to a reference value. In some embodiments, the method includes detecting a decrease, such as a statistically significant decrease, such as at least a 2, 3, 4, or 5 fold decrease in the amount of one or more protein antigens listed in Table 2, flagellin, BipC, LPS, CPS and/or EPS of *B. pseudomallei* as compared to a reference sample.

In one embodiment, the method includes comparing a proteomic profile of a test sample of urine from a subject of interest comprising at least one of protein associated with melioidosis, such a protein antigen listed in Table 2, flagellin, BipC, of LPS, CPS and/or EPS of *B. pseudomallei* or all of these molecules with a proteomic profile from a reference sample.

In one embodiment, the method determines if the subject has melioidosis. If the reference sample is a normal sample and the proteomic profile of the test sample is essentially the same as the proteomic profile of the normal sample, the subject is determined not to have melioidosis. However, if the proteomic profile of the test sample has a unique expression signature relative to the proteomic profile of the normal sample the subject is determined to have melioidosis.

In some embodiments, if the reference sample is a sample from a subject with melioidosis, and its proteomic profile shares at least one unique expression signature characteristic with the reference sample, then the subject is determined to have melioidosis. If the proteomic profile of the test sample has a unique expression signature relative to the reference sample the subject is determined not to have melioidosis. Hence, the proteomic profile provides an additional diagnostic criterion for these disorders.

In one embodiment, the method is a method to determine if a therapy is effective for the treatment of the subject by detecting the presence of at least one protein associated with melioidosis. The method can be performed multiple times over a specified time period, such as days, weeks, months or years. In several examples, the therapy includes treatment with a therapeutic agent for melioidosis. If the reference sample is a normal sample, and the proteomic profile of the test sample is essentially the same as the proteomic profile of the normal sample the subject is determined to have an effective therapy, while if the proteomic profile of the test sample has a unique expression signature relative to the proteomic profile of the normal sample to have an ineffective therapy. If the reference sample is a sample from a subject with melioidosis, and proteomic profile shares at least one unique expression signature characteristic with the reference sample then the subject is determined to have an ineffective therapy, while if the proteomic profile of the test sample has a unique expression signature relative to the reference sample the subject is determined to have an effective therapy. Changes in the profile can also represent the progression (or regression) of the disease process. Methods for monitoring the efficacy of therapeutic agents are described below.

Monitoring

The diagnostic methods of the present disclosure are valuable tools for practicing physicians to make quick treatment decisions for melioidosis conditions, including both acute and chronic melioidosis. These treatment decisions can include the administration of an anti-melioidosis agent and decisions to monitor a subject for onset and/or advancement of melioidosis. The method disclosed herein can also be used to monitor the effectiveness of a therapy.

Following the measurement of the expression levels of one or more of the molecules identified herein, the assay results, findings, diagnoses, predictions and/or treatment recommendations are typically recorded and communicated to technicians, physicians and/or patients, for example. In certain embodiments, computers will be used to communicate such information to interested parties, such as, patients and/or the attending physicians. Based on the measurement, the therapy administered to a subject can be modified.

In one embodiment, a diagnosis, prediction and/or treatment recommendation based on the expression level in a test subject of one or more of the melioidosis associated molecules disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having melioidosis results in the physician treating the subject, such as prescribing one or more therapeutic agents for inhibiting or delaying one or more signs and symptoms associated with melioidosis. In additional embodiments, the dose or dosing regimen is modified based on the information obtained using the methods disclosed herein.

The subject can be monitored while undergoing treatment using the methods described herein in order to assess the efficacy of the treatment protocol. In this manner, the length of time or the amount give to the subject can be modified based on the results obtained using the methods disclosed herein.

III. Immunoassays for Diagnosing and Monitoring Melioidosis

The methods disclosed herein can be performed in the form of various immunoassay formats, which are well known in the art. There are two main types of immunoassays, homogeneous and heterogeneous. In homogeneous immunoassays, both the immunological reaction between an antigen and an antibody and the detection are carried out in a homogeneous reaction. Heterogeneous immunoassays include at least one separation step, which allows the differentiation of reaction products from unreacted reagents. A variety of immunoassays can be used to detect one or more of the molecules capable of detecting melioidosis, including detecting extracellular polysaccharides. In one example, one or more antigens associated with melioidosis are measured to diagnose melioidosis. For example, one or more protein antigens listed in Table 2, flagellin, BipC, EPS, CPS, LPS or a combination thereof are detected with a disclosed immunoassay. In one example, at least GroEL is detected with the disclosed immunoassay. In one example, at least GroEL, flagellin and BipC are detected.

ELISA is a heterogeneous immunoassay, which has been widely used in laboratory practice since the early 1970s, and can be used in the methods disclosed herein. The assay can be used to detect protein antigens in various formats. In the "sandwich" format the antigen being assayed is held between two different antibodies. In this method, a solid surface is first coated with a solid phase antibody. The test sample, containing the antigen (e.g., a diagnostic protein), or a composition containing the antigen, such as a urine sample from a subject of interest, is then added and the antigen is allowed to react with the bound antibody. Any unbound antigen is washed away. A known amount of enzyme-labeled antibody is then allowed to react with the bound antigen. Any excess unbound enzyme-linked antibody is washed away after the reaction. The substrate for the enzyme used in the assay is then added and the reaction between the substrate and the enzyme produces a color change. The amount of visual color change is a direct measurement of specific enzyme-conjugated bound antibody, and consequently the antigen present in the sample tested.

ELISA can also be used as a competitive assay. In the competitive assay format, the test specimen containing the antigen to be determined is mixed with a precise amount of enzyme-labeled antigen and both compete for binding to an anti-antigen antibody attached to a solid surface. Excess free enzyme-labeled antigen is washed off before the substrate for the enzyme is added. The amount of color intensity resulting from the enzyme-substrate interaction is a measure of the amount of antigen in the sample tested. A heterogenous immunoassay, such as an ELISA, can be used to detect any molecules associated with melioidosis.

In another example, immuno-PCR can be used to detect any of the molecules associated with melioidosis, such as the exopolysaccharide (EPS), the capsular polysaccharide (CPS), and the lipopolysaccharide (LPS) for *B. pseudomallei*. Immuno-PCR is a modification of the conventional ELISA format in which the detecting antibody is labeled with a DNA label, and is applicable to the analysis of biological samples (see, e.g., U.S. Pat. No. 5,665,539 and U.S. Patent Application Publication No. 2005/0239108; all herein incorporated by reference). The amplification ability of PCR provides large amounts of the DNA label which can be detected by various methods, typically gel electrophoresis with conventional staining (e.g., Sano et al., *Science,* 258:120-122, 1992). This method can also include the direct conjugation of the DNA label to the antibody and replacement of gel electrophoresis by using labeled primers to generate a PCR product that can be assayed by ELISA or using real time quantitative PCR. In an example of the real-time PCR method, PCR is used to amplify DNA in a sample in the presence of a nonextendable dual labeled fluorogenic hybridization probe. One fluorescent dye serves as a reporter and its emission spectra is quenched by the second fluorescent dye. The method uses the 5' nuclease activity of Taq polymerase to cleave a hybridization probe during the extension phase of PCR. The nuclease degradation of the hybridization probe releases the quenching of the reporter dye resulting in an increase in peak emission from the reporter. The reactions are monitored in real time.

Homogeneous immunoassays include, for example, the Enzyme Multiplied Immunoassay Technique (EMIT), which typically includes a biological sample comprising the biomarkers to be measured, enzyme-labeled molecules of the biomarkers to be measured, specific antibody or antibodies binding the biomarkers to be measured, and a specific enzyme chromogenic substrate. In a typical EMIT, excess of specific antibodies is added to a biological sample. If the biological sample contains the molecules to be detected, such molecules bind to the antibodies. A measured amount of the corresponding enzyme-labeled molecules is then added to the mixture. Antibody binding sites not occupied by molecules of the protein in the sample are occupied with molecules of the added enzyme-labeled protein. As a result, enzyme activity is reduced because only free enzyme-labeled protein can act on the substrate. The amount of substrate converted from a colorless to a colored form determines the amount of free enzyme left in the mixture. A high concentration of the protein to be detected in the sample causes higher absorbance readings. Less protein in the sample results in less enzyme activity and consequently lower absorbance readings. Inactivation of the enzyme label when the antigen-enzyme complex is antibody-bound makes the EMIT a useful system, enabling the test to be performed without a separation of bound from unbound compounds as is necessary with other immunoassay methods. A homogenous immunoassay, such as an EMIT, can be used to detect any of the molecules associated with melioidosis, such as protein antigens listed in Table 2 (such as GroEL), flagellin, BipC, EPS, CPS, LPS or a combination thereof.

Immunoassay kits are also disclosed herein. These kits include, in separate containers (a) monoclonal antibodies having binding specificity for the polypeptides used in the diagnosis of melioidosis; and (b) and anti-antibody immunoglobulins. This immunoassay kit may be utilized for the practice of the various methods provided herein. The monoclonal antibodies and the anti-antibody immunoglobulins can be provided in an amount of about 0.001 mg to 100 grams, and more preferably about 0.01 mg to 1 gram. The anti-antibody immunoglobulin may also be a polyclonal immunoglobulin, protein A or protein G or functional fragments thereof, which may be labeled prior to use by methods known in the art. In several embodiments, the immunoassay kit includes one, two, three or four antibodies that specifically bind to molecules associated with melioidosis, such as protein antigens listed in Table 2, flagellin, BipC, EPS, CPS and LPS. The immunoassay kit can also include one or more antibodies that specifically bind to one or more of these molecules. Thus, the kits can be used to detect one or more different molecules associated with melioidosis.

Immunoassays for polysaccharides and proteins differ in that a single antibody is used for both the capture and indicator roles for polysaccharides due to the presence of repeating epitopes. In contrast, two antibodies specific for distinct epitopes are required for immunoassay of proteins. Exemplary samples include biological samples obtained from subjects including, but not limited to, serum and urine samples.

In one particular example, a quantitative ELISA is constructed for detection of at least one of the protein antigens listed in Table 2, flagellin, BipC, EPS, CPS, LPS CPS, EPS, LPS or a combination thereof. These immunoassays utilize antibodies, such as mAbs commercially available or disclosed herein. Since a polysaccharide is a polyvalent repeating structure, a single mAb is used for both the capture and indicator phases of an immunoassay. The only requirement is that the mAb have a sufficient affinity. A mAb with an affinity of about 0.5 µM has sufficient affinity.

IV. Capture Device Methods

The disclosed methods can be carried out using a sample capture device, such as a lateral flow device (for example a lateral flow test strip) that allows detection of one or more molecules, such as those described herein.

Point-of-use analytical tests have been developed for the routine identification or monitoring of health-related conditions (such as pregnancy, cancer, endocrine disorders, infectious diseases or drug abuse) using a variety of biological samples (such as urine, serum, plasma, blood, saliva). Some of the point-of-use assays are based on highly specific interactions between specific binding pairs, such as antigen/antibody, hapten/antibody, lectin/carbohydrate, apoprotein/cofactor and biotin/(strept)avidin. The assays are often performed with test strips in which a specific binding pair member is attached to a mobilizable material (such as a metal sol or beads made of latex or glass) or an immobile substrate (such as glass fibers, cellulose strips or nitrocellulose membranes). Particular examples of some of these assays are shown in U.S. Pat. Nos. 4,703,017; 4,743,560; and 5,073,484 (incorporated herein by reference). The test strips include a flow path from an upstream sample application area to a test site. For example, the flow path can be from a sample application area through a mobilization zone to a capture zone. The mobilization zone may contain a mobilizable marker that interacts with an analyte or analyte analog, and the capture zone contains a reagent that binds the analyte or analyte analog to detect the presence of an analyte in the sample.

Examples of migration assay devices, which usually incorporate within them reagents that have been attached to colored labels, thereby permitting visible detection of the assay results without addition of further substances are found, for example, in U.S. Pat. No. 4,770,853; WO 88/08534; and EP-A 0 299 428 (incorporated herein by reference). There are a number of commercially available lateral-flow type tests and patents disclosing methods for the detection of large analytes (MW greater than 1,000 Daltons) as the analyte flows through multiple zones on a test strip. Examples are found in U.S. Pat. No. 5,229,073 (measuring plasma lipoprotein levels), and U.S. Pat. Nos. 5,591,645; 4,168,146; 4,366, 241; 4,855,240; 4,861,711; 5,120,643; European Patent No. 0296724; WO 97/06439; WO 98/36278; and WO 08/030,546 (each of which are herein incorporated by reference). Multiple zone lateral flow test strips are disclosed in U.S. Pat. Nos. 5,451,504, 5,451,507, and 5,798,273 (incorporated by reference herein). U.S. Pat. No. 6,656,744 (incorporated by reference) discloses a lateral flow test strip in which a label binds to an antibody through a streptavidin-biotin interaction.

In particular examples, the methods disclosed herein include application of a biological sample (such as serum or urine) from a test subject to a lateral flow test device for the detection of one or more molecules (such as one or more molecules associated with meliosidosis, for example, combinations of molecules as described above) in the sample. The lateral flow test device includes one or more antibodies (such as antibodies that bind one or more of the molecules associated with meliosidosis) at an addressable location. In a particular example, the lateral flow test device includes antibodies that bind at least one protein antigen listed in Table 2, flagellin, BipC, EPS, CPS, LPS or a combination thereof. The addressable locations can be, for example, a linear array or other geometric pattern that provides diagnostic information to the user. The binding of one or more molecules in the sample to the antibodies present in the test device is detected and the presence or amount of one or more molecules in the sample of the test subject is compared to a control, wherein a change in the presence or amount of one or more molecules in the sample from the test subject as compared to the control indicates that the subject has melioidosis.

Flow-through Devices

Flow-through type assay devices were designed, in part, to obviate the need for incubation and washing steps associated with dipstick assays. Flow-through immunoassay devices involve a capture reagent (such as one or more antibodies) bound to a porous membrane or filter to which a liquid sample is added. As the liquid flows through the membrane, target analyte (such as protein) binds to the capture reagent. The addition of sample is followed by (or made concurrent with) addition of detector reagent, such as labeled (e.g., gold-conjugated or colored latex particle-conjugated protein). Alternatively, the detector reagent may be placed on the membrane in a manner that permits the detector to mix with the sample and thereby label the analyte. The visual detection of detector reagent provides an indication of the presence of target analyte in the sample. Representative flow-through assay devices are described in U.S. Pat. Nos. 4,246,339; 4,277,560; 4,632, 901; 4,812,293; 4,920,046; and 5,279,935; U.S. Patent Application Publication Nos. 20030049857 and 20040241876; and WO 08/030,546. Migration assay devices usually incorporate within them reagents that have been attached to colored labels, thereby permitting visible detection of the assay results without addition of further substances. See, for example, U.S. Pat. No. 4,770,853; PCT Publication No. WO 88/08534 and European Patent No. EP-A 0 299 428.

There are a number of commercially available lateral flow type tests and patents disclosing methods for the detection of large analytes (MW greater than 1,000 Daltons). U.S. Pat. No. 5,229,073 describes a semiquantitative competitive immunoassay lateral flow method for measuring plasma lipoprotein levels. This method utilizes a plurality of capture zones or lines containing immobilized antibodies to bind both the labeled and free lipoprotein to give a semi-quantitative result. In addition, U.S. Pat. No. 5,591,645 provides a chromatographic test strip with at least two portions. The first portion includes a movable tracer and the second portion includes an immobilized binder capable of binding to the analyte. Additional examples of lateral flow tests for large analytes are disclosed in the following patent documents: U.S. Pat. Nos. 4,168,146; 4,366,241; 4,855,240; 4,861,711; and 5,120,643; European Patent No. 0296724; WO 97/06439; WO 98/36278; and WO 08/030,546.

Devices described herein generally include a strip of absorbent material (such as a microporous membrane), which, in some instances, can be made of different substances each joined to the other in zones, which may be abutted and/or overlapped. In some examples, the absorbent strip can be fixed on a supporting non-interactive material (such as non-woven polyester), for example, to provide increased rigidity to the strip. Zones within each strip may differentially contain the specific binding partner(s) and/or other reagents required for the detection and/or quantification of the particular analyte being tested for, for example, one or more molecules disclosed herein. Thus these zones can be viewed as functional sectors or functional regions within the test device.

In general, a fluid sample is introduced to the strip at the proximal end of the strip, for instance by dipping or spotting. A sample is collected or obtained using methods well known to those skilled in the art. The sample containing the particular molecules to be detected may be obtained from any biological source. Examples of biological sources include blood serum, blood plasma, urine, spinal fluid, saliva, fermentation fluid, lymph fluid, tissue culture fluid and ascites fluid of a human or animal. In a particular example, the biological source is saliva. The sample may be diluted, purified, concentrated, filtered, dissolved, suspended or otherwise manipulated prior to assay to optimize the immunoassay results. The fluid migrates distally through all the functional regions of the strip. The final distribution of the fluid in the individual functional regions depends on the adsorptive capacity and the dimensions of the materials used.

In some embodiments, porous solid supports, such as nitrocellulose, described hereinabove are preferably in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 62.5 sec/cm (i.e., 250 sec/4 cm). In other specific embodiments of devices described herein, the flow rate is about 37.5 sec/cm (i.e., 150 sec/4 cm).

Another common feature to be considered in the use of assay devices is a means to detect the formation of a complex between an analyte (such as one or more molecules described herein) and a capture reagent (such as one or more antibodies). A detector (also referred to as detector reagent) serves this purpose. A detector may be integrated into an assay device (for example included in a conjugate pad, as described below), or may be applied to the device from an external source.

A detector may be a single reagent or a series of reagents that collectively serve the detection purpose. In some instances, a detector reagent is a labeled binding partner specific for the analyte (such as a gold-conjugated antibody for a particular protein of interest, for example those described herein).

In other instances, a detector reagent collectively includes an unlabeled first binding partner specific for the analyte and a labeled second binding partner specific for the first binding partner and so forth. Thus, the detector can be a labeled antibody specific for a protein described herein. The detector can also be an unlabeled first antibody specific for the protein of interest and a labeled second antibody that specifically binds the unlabeled first antibody. In each instance, a detector reagent specifically detects bound analyte of an analyte-capture reagent complex and, therefore, a detector reagent preferably does not substantially bind to or react with the capture reagent or other components localized in the analyte capture area. Such non-specific binding or reaction of a detector may provide a false positive result. Optionally, a detector reagent can specifically recognize a positive control molecule (such as a non-specific human IgG for a labeled Protein A detector, or a labeled Protein G detector, or a labeled anti-human Ab(Fc)) that is present in a secondary capture area.

Flow-Through Device Construction and Design

A flow-through device involves a capture reagent (such as one or more antibodies) immobilized on a solid support, typically, microtiter plate or a membrane (such as, nitrocellulose, nylon, or PVDF). Characteristics of useful membrane have been previously described; however, it is useful to note that in a flow-through assay capillary rise is not a particularly important feature of a membrane as the sample moves vertically through the membrane rather than across it as in a lateral flow assay. In a simple representative format, the membrane of a flow-through device is placed in functional or physical contact with an absorbent layer (see, e.g., description of "absorbent pad" below), which acts as a reservoir to draw a fluid sample through the membrane. Optionally, following immobilization of a capture reagent, any remaining protein-binding sites on the membrane can be blocked (either before or concurrent with sample administration) to minimize non-specific interactions.

In operation of a flow-through device, a fluid sample (such as a bodily fluid sample) is placed in contact with the membrane. Typically, a flow-through device also includes a sample application area (or reservoir) to receive and temporarily retain a fluid sample of a desired volume. The sample passes through the membrane matrix. In this process, an analyte in the sample (such as one or more protein, for example, one or more molecules described herein) can specifically bind to the immobilized capture reagent (such as one or more antibodies). Where detection of an analyte-capture reagent complex is desired, a detector reagent (such as labeled antibodies that specifically bind one or more molecules) can be added with the sample or a solution containing a detector reagent can be added subsequent to application of the sample. If an analyte is specifically bound by capture reagent, a visual representative attributable to the particular detector reagent can be observed on the surface of the membrane. Optional wash steps can be added at any time in the process, for instance, following application of the sample, and/or following application of a detector reagent.

Lateral Flow Device Construction and Design

Lateral flow devices are commonly known in the art. Briefly, a lateral flow device is an analytical device having as its essence a test strip, through which flows a test sample fluid that is suspected of containing an analyte of interest. The test fluid and any suspended analyte can flow along the strip to a detection zone in which the analyte (if present) interacts with a capture agent and a detection agent to indicate a presence, absence and/or quantity of the analyte.

Numerous lateral flow analytical devices have been disclosed, and include those shown in U.S. Pat. Nos. 4,313,734; 4,435,504; 4,775,636; 4,703,017; 4,740,468; 4,806,311; 4,806,312; 4,861,711; 4,855,240; 4,857,453; 4,943,522; 4,945,042; 4,496,654; 5,001,049; 5,075,078; 5,126,241; 5,451,504; 5,424,193; 5,712,172; 6,555,390; 6,258,548; 6,699,722; 6,368,876 and 7,517,699; EP 0810436; and WO 92/12428; WO 94/01775; WO 95/16207; and WO 97/06439, each of which is incorporated by reference.

Many lateral flow devices are one-step lateral flow assays in which a biological fluid is placed in a sample area on a bibulous strip (though non-bibulous materials can be used, and rendered bibulous, e.g., by applying a surfactant to the material), and allowed to migrate along the strip until the liquid comes into contact with a specific binding partner (such as an antibody) that interacts with an analyte (such as one or more molecules) in the liquid. Once the analyte interacts with the binding partner, a signal (such as a fluorescent or otherwise visible dye) indicates that the interaction has occurred. Multiple discrete binding partners (such as antibodies) can be placed on the strip (for example in parallel lines) to detect multiple analytes (such as two or more molecules) in the liquid. The test strips can also incorporate control indicators, which provide a signal that the test has adequately been performed, even if a positive signal indicating the presence (or absence) of an analyte is not seen on the strip.

The construction and design of lateral flow devices is very well known in the art, as described, for example, in Millipore Corporation, *A Short Guide Developing Immunochromatographic Test Strips,* 2nd Edition, pp. 1-40, 1999, available by request at (800) 645-5476; and Schleicher & Schuell, *Easy to Work with BioScience, Products and Protocols* 2003, pp. 73-98, 2003, 2003, available by request at Schleicher & Schuell BioScience, Inc., 10 Optical Avenue, Keene, N.H. 03431, (603) 352-3810; both of which are incorporated herein by reference.

Lateral flow devices have a wide variety of physical formats that are equally well known in the art. Any physical format that supports and/or houses the basic components of a lateral flow device in the proper function relationship is contemplated by this disclosure.

Figure 9A:
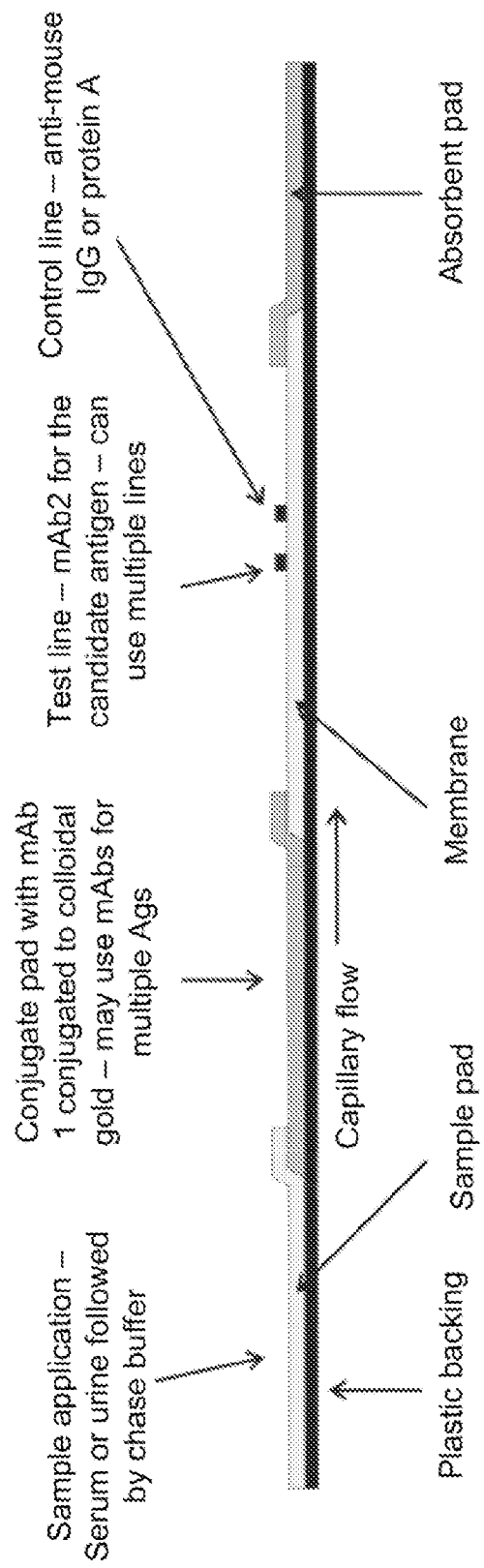
Figure 9B:
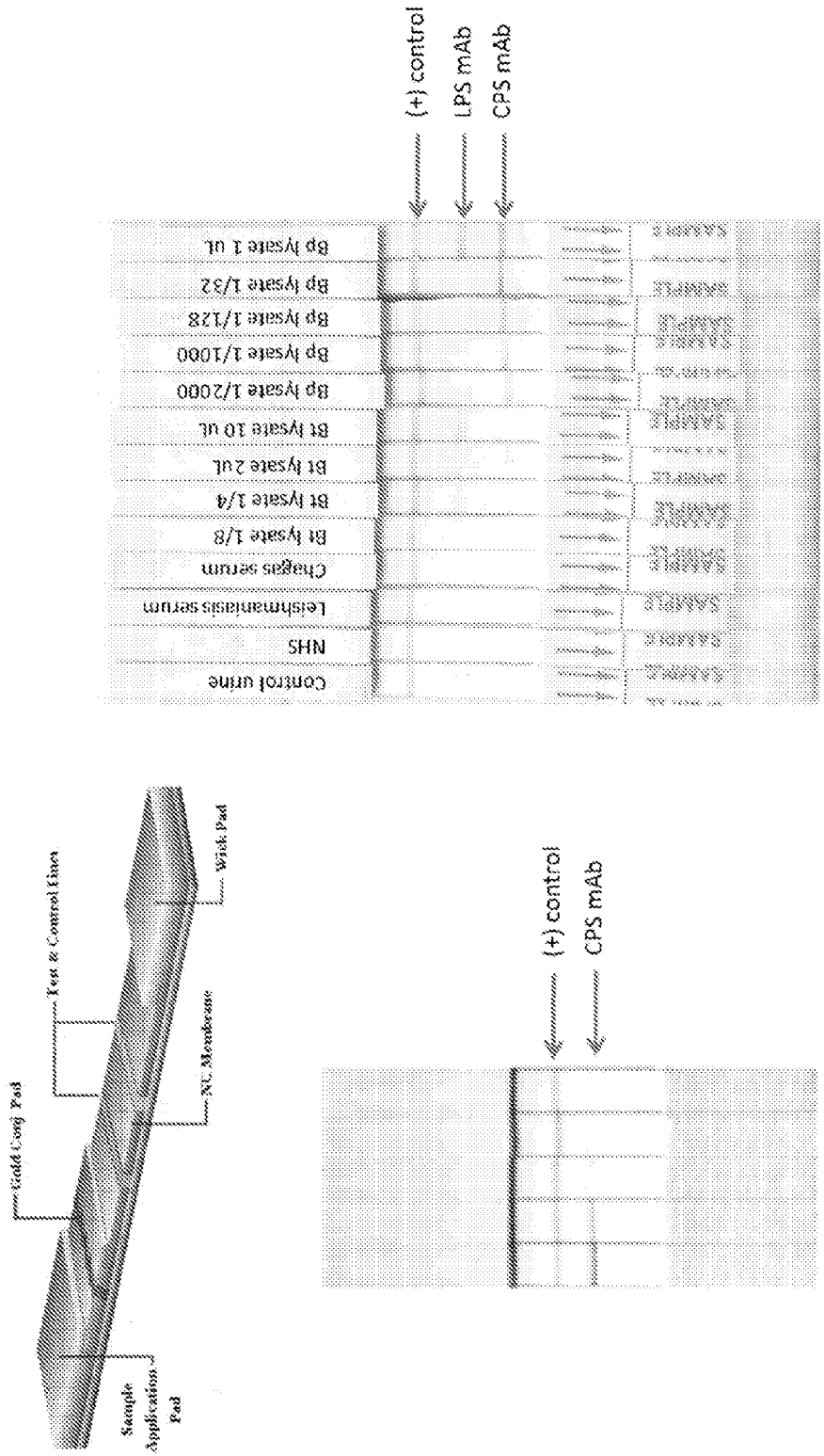
Figure 9C:
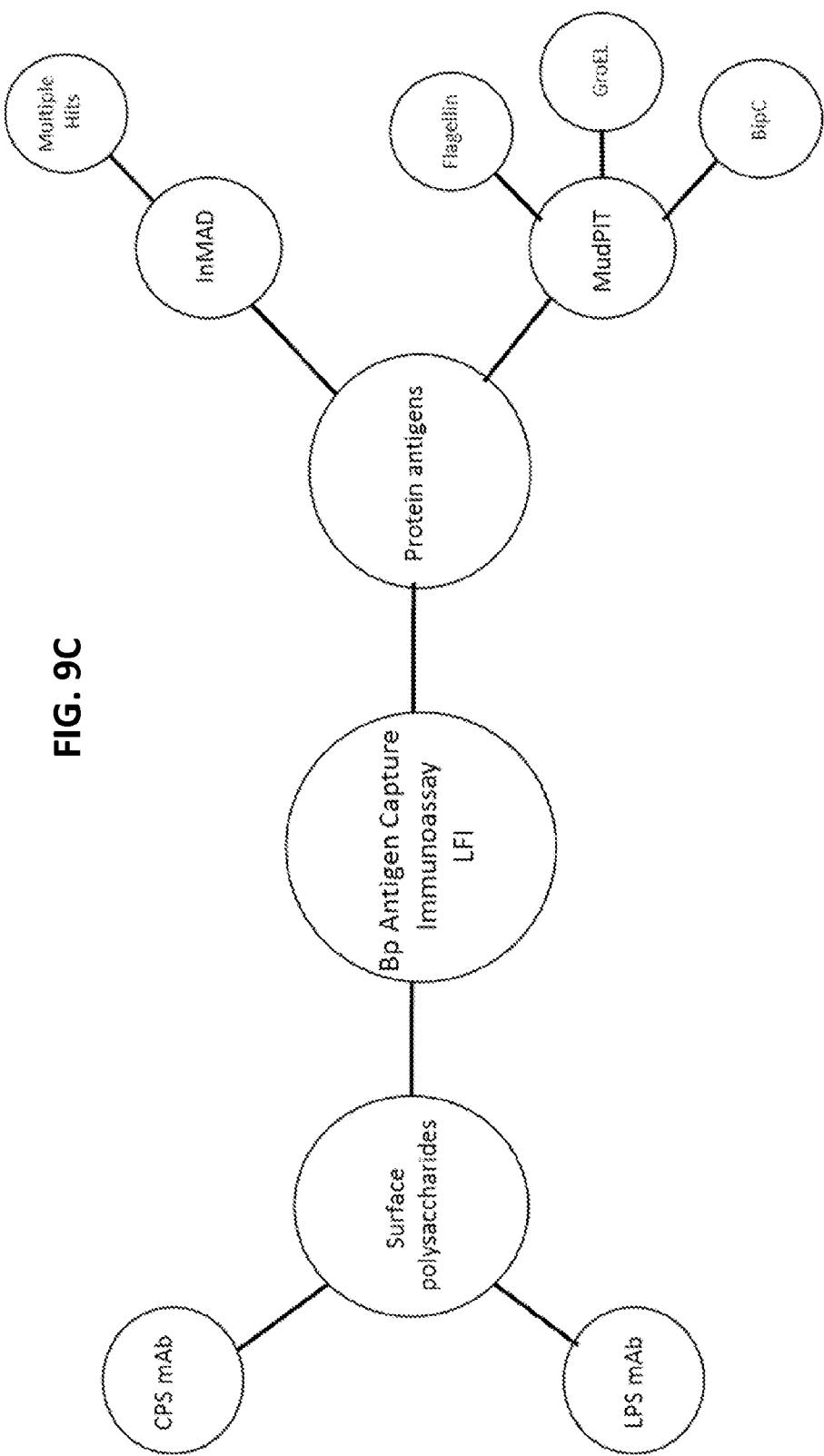
Figure 12:
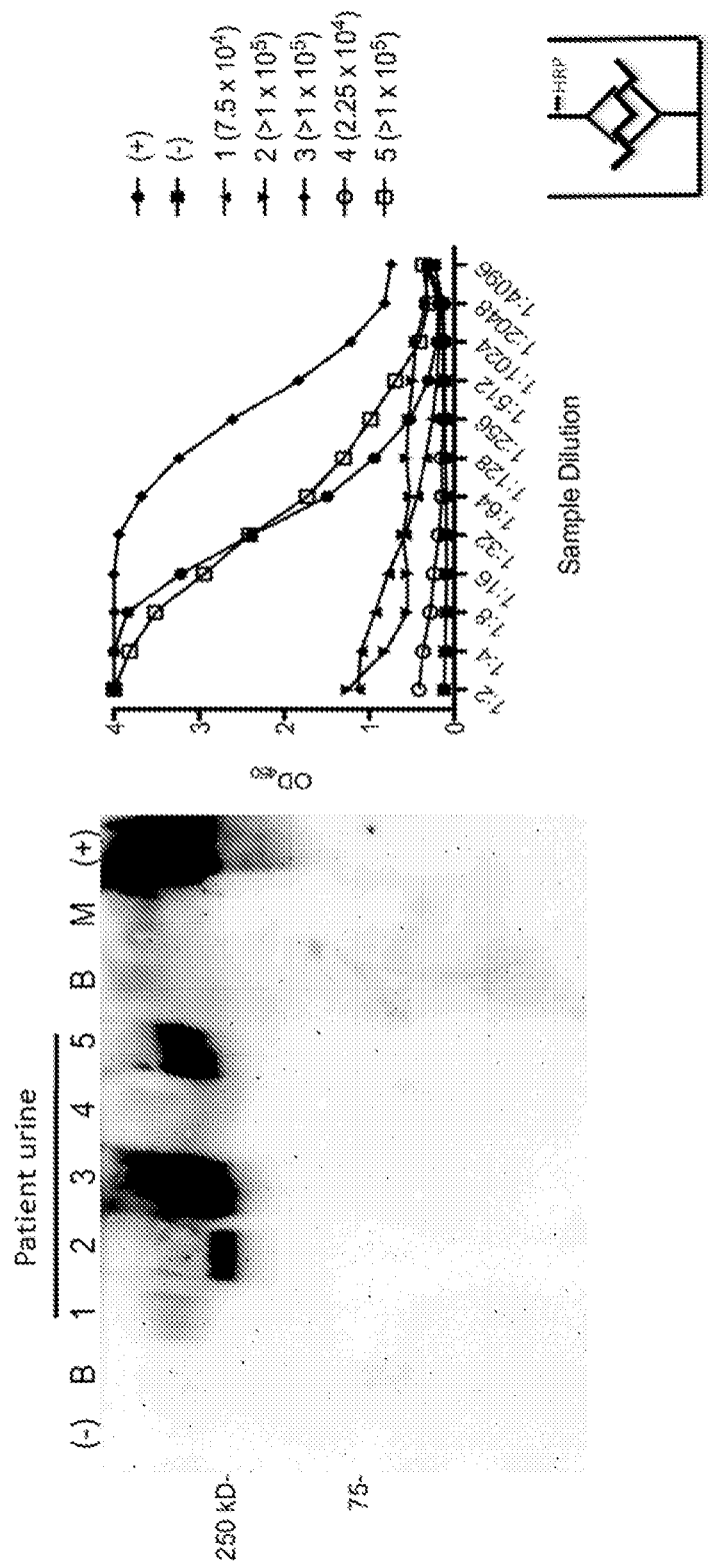
FIG. 12 is a digital image of a Western blot analysis illustrating detection of CPS in urine samples from subjects with melioidosis.
Figure 13:
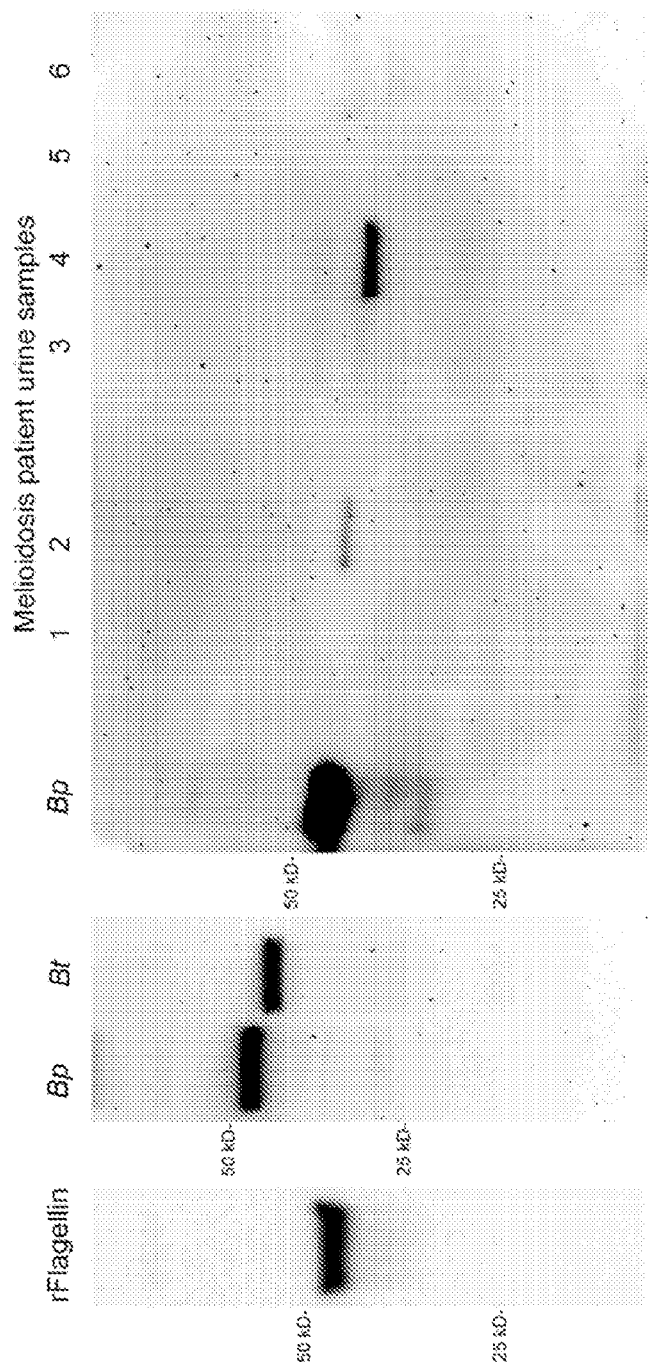
FIG. 13 is a digital image of a Western blot analysis illustrating detection of flagellin in urine samples from subjects with melioidosis.
Figure 14:
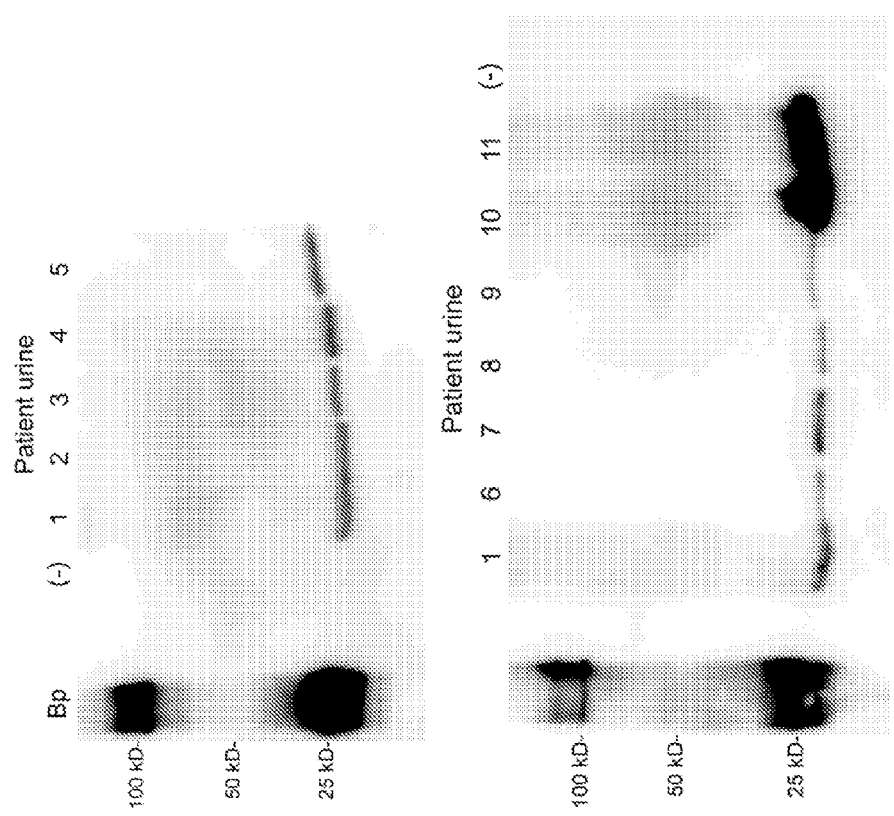
FIG. 14 is a digital image of a Western blot analysis illustrating detection of GroEL in urine samples from subjects with melioidosis.
Figure 15:
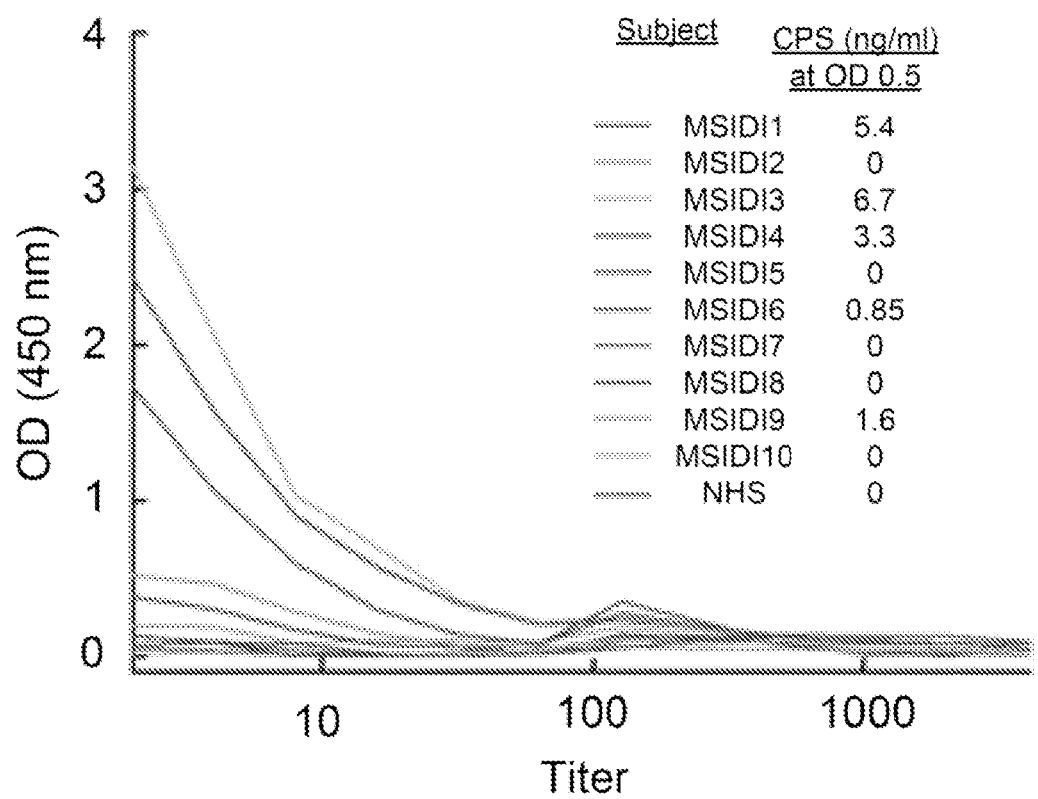
FIG. 15 is a tracing illustrating detection of *B. pseudomallei* CPS in patient serum samples. An antigen capture ELISA was performed with mAb 3C5 in the solid phase followed by incubation of patient serum (MSID1-10). Following washing steps HRP-labeled 3C5 was used to detect CPS. NHS (normal human serum).

The basic components of exemplary lateral flow devices are illustrated in FIG. 9. In some embodiments, the lateral flow strip is divided into a proximal sample application pad, an intermediate test result zone, and a distal absorbent pad. The flow strip is interrupted by a conjugate pad that contains labeled conjugate (such as gold- or latex-conjugated antibody specific for the target analyte or an analyte analog). A flow path along strip passes from proximal pad, through conjugate pad, into test result zone, for eventual collection in absorbent pad. Selective binding agents are positioned on a proximal test line in the test result membrane. A control line is provided in test result zone, slightly distal to the test line. For example, in a competitive assay, the binding agent in the test line specifically binds the target analyte, while the control line less specifically binds the target analyte.

In operation of the particular embodiment of a lateral flow device illustrated in FIG. 9, a fluid sample containing an analyte of interest, such as one or more molecules described herein (for example, protein antigens listed in Table 2, flagellin, BipC, EPS, CPS, LPS CPS, LPS or EPS or other combinations of molecules, as discussed above), is applied to the sample pad. In some examples, the sample may be applied to the sample pad by dipping the end of the device containing the sample pad into the sample (such as serum or urine) or by applying the sample directly onto the sample pad (for example by placing the sample pad in the mouth of the subject). In other examples where a sample is whole blood, an optional developer fluid is added to the blood sample to cause hemolysis of the red blood cells and, in some cases, to make an appropriate dilution of the whole blood sample.

From the sample pad, the sample passes, for instance by capillary action, to the conjugate pad. In the conjugate pad, the analyte of interest, such as a protein of interest, may bind (or be bound by) a mobilized or mobilizable detector reagent, such as an antibody (such as antibody that recognizes one or more of the molecules described herein). For example, a protein analyte may bind to a labeled (e.g., gold-conjugated or colored latex particle-conjugated) antibody contained in the conjugate pad. The analyte complexed with the detector reagent may subsequently flow to the test result zone where the complex may further interact with an analyte-specific binding partner (such as an antibody that binds a particular protein, an anti-hapten antibody, or streptavidin), which is immobilized at the proximal test line. In some examples, a protein complexed with a detector reagent (such as gold-conjugated antibody) may further bind to unlabeled, oxidized antibodies immobilized at the proximal test line. The formation of a complex, which results from the accumulation of the label (e.g., gold or colored latex) in the localized region of the proximal test line is detected. The control line may contain an immobilized, detector-reagent-specific binding partner, which can bind the detector reagent in the presence or absence of the analyte. Such binding at the control line indicates proper performance of the test, even in the absence of the analyte of interest. The test results may be visualized directly, or may measured using a reader (such as a scanner). The reader device may detect color or fluorescence from the readout area (for example, the test line and/or control line).

In another embodiment of a lateral flow device, there may be a second (or third, fourth, or more) test line located parallel or perpendicular (or in any other spatial relationship) to test line in test result zone. The operation of this particular embodiment is similar to that described in the immediately preceding paragraph with the additional considerations that (i) a second detector reagent specific for a second analyte, such as another antibody, may also be contained in the conjugate pad, and (ii) the second test line will contain a second specific binding partner having affinity for a second analyte, such as a second protein in the sample. Similarly, if a third (or more) test line is included, the test line will contain a third (or more) specific binding partner having affinity for a third (or more) analyte.

1. Sample Pad

The sample pad is a component of a lateral flow device that initially receives the sample, and may serve to remove particulates from the sample. Among the various materials that may be used to construct a sample pad (such as glass fiber, woven fibers, screen, non-woven fibers, cellosic fibers or paper), a cellulose sample pad may be beneficial if a large bed volume (e.g., 250 μl/cm$^2$) is a factor in a particular application. Sample pads may be treated with one or more release agents, such as buffers, salts, proteins, detergents, and surfactants. Such release agents may be useful, for example, to promote resolubilization of conjugate-pad constituents, and to block non-specific binding sites in other components of a lateral flow device, such as a nitrocellulose membrane. Representative release agents include, for example, trehalose or glucose (1%-5%), PVP or PVA (0.5%-2%), Tween 20 or Triton X-100 (0.1%-1%), casein (1%-2%), SDS (0.02%-5%), and PEG (0.02%-5%).

2. Membrane and Application Solution:

The types of membranes useful in a lateral flow device (such as nitrocellulose (including pure nitrocellulose and modified nitrocellulose), nitrocellulose direct cast on polyester support, polyvinylidene fluoride, or nylon), and considerations for applying a capture reagent to such membranes have been discussed previously.

3. Conjugate Pad

The conjugate pad serves to, among other things, hold a detector reagent. Suitable materials for the conjugate pad include glass fiber, polyester, paper, or surface modified polypropylene. In some embodiments, a detector reagent may be applied externally, for example, from a developer bottle, in which case a lateral flow device need not contain a conjugate pad (see, for example, U.S. Pat. No. 4,740,468).

Detector reagent(s) contained in a conjugate pad is typically released into solution upon application of the test sample. A conjugate pad may be treated with various substances to influence release of the detector reagent into solution. For example, the conjugate pad may be treated with PVA or PVP (0.5% to 2%) and/or Triton X-100 (0.5%). Other release agents include, without limitation, hydroxypropylmethyl cellulose, SDS, Brij and β-lactose. A mixture of two or more release agents may be used in any given application. In a particular disclosed embodiment, the detector reagent in conjugate pad is a gold-conjugated antibody.

4. Absorbent Pad

The use of an absorbent pad in a lateral flow device is optional. The absorbent pad acts to increase the total volume of sample that enters the device. This increased volume can be useful, for example, to wash away unbound analyte from the membrane. Any of a variety of materials is useful to prepare an absorbent pad, for example, cellulosic filters or paper. In some device embodiments, an absorbent pad can be paper (i.e., cellulosic fibers). One of skill in the art may select a paper absorbent pad on the basis of, for example, its thickness, compressibility, manufacturability, and uniformity of bed volume. The volume uptake of an absorbent made may be adjusted by changing the dimensions (usually the length) of an absorbent pad.

V. Methods for Inducing an Immune Response

Methods of inducing an immune response to melioidosis are also disclosed. The methods include the use of the immunogenic melioidosis polypeptides disclosed herein, nucleic acids encode these polypeptides, and/or viral vectors encoding an immunogenic melioidosis polypeptide, alone or in conjunction with other agents, such as traditional melioidosis therapies. In several embodiments, the methods include administering to a subject with melioidosis a therapeutically effective amount of one or more melioidosis polypeptides disclosed herein, in order to generate an immune response.

The methods can include selecting a subject in need of treatment, such as a subject having or at risk acquiring melioidosis. In exemplary applications, compositions are administered to a subject having a disease, such as melioidosis, in an amount sufficient to raise an immune response to melioidosis-associated antigen-expressing cells. Administration induces a sufficient immune response to slow the proliferation of such cells or to inhibit their growth, or to reduce a sign or a symptom of melioidosis. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

A melioidosis polypeptide can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) either locally or systemically, such as by intramuscular, subcutaneous, intraperitoneal or intravenous injection, but even oral, nasal, transdermal or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

In one specific, non-limiting example, the melioidosis polypeptide is administered in a manner to direct the immune response to a cellular response (that is, a cytotoxic T lymphocyte (CTL) response), rather than a humoral (antibody) response.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, OX-40L, 41 BBL and ICAM-1 are administered.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. Further, as the induction of neutralizing antibodies can also be primed with the same molecule conjugated to a peptide which displays an appropriate epitope, two compositions can be combined to elicit both humoral and cell-mediated responses where that is deemed desirable.

In yet another embodiment, to induce a CTL response to an immunogenic melioidosis polypeptide, a MHC Class II-restricted T-helper epitope is added to the immunogenic melioidosis polypeptide to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," in Powell et al., eds., *Vaccine Design, the Subunit and Adjuvant Approach*, Plenum Press, New York, 1995).

A pharmaceutical composition including a melioidosis polypeptide is thus provided. These compositions are use to generate an immune response, such as for immunotherapy. In one embodiment, a melioidosis polypeptide is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, e.g., Schmolka, *J. Am. Oil. Chem. Soc.* 54:110, 1977, and Hunter et al., *J. Immunol.* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

In one embodiment, the adjuvant is a mixture of stabilizing detergents, micelle-forming agent, and oil available under the name PROVAX® (IDEC Pharmaceuticals, San Diego, Calif.). An adjuvant can also be an immunostimulatory nucleic acid, such as a nucleic acid including a CpG motif, or a biological adjuvant (see above).

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa., 1995. Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342, 1994; Tice & Tabibi, *Treatise on Controlled Drug Delivery*, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

In another embodiment, a pharmaceutical composition includes a nucleic acid encoding a melioidosis polypeptide. A therapeutically effective amount of the melioidosis polynucleotide can be administered to a subject in order to generate an immune response. In one specific, non-limiting example, a therapeutically effective amount of the melioidosis polynucleotide is administered to a subject to treat one or more signs and symptoms associated with melioidosis.

Optionally, one or more cytokines, such as IL-2, IL-6, IL-12, RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, J. Surg. Oncol. 68(2):122-38; Lotze et al., 2000, Cancer J. Sci. Am. 6(Suppl 1):S61-6; Cao et al., 1998, Stem Cells 16(Suppl 1):251-60; Kuiper et al., 2000, Adv. Exp. Med. Biol. 465:381-90). These molecules can be administered systemically to the host. It should be noted that these molecules can be co-administered via insertion of a nucleic acid encoding the molecules into a vector, for example, a recombinant pox vector (see, for example, U.S. Pat. No. 6,045,802). In various embodiments, the nucleic acid encoding the biological adjuvant can be cloned into same vector as the melioidosis polypeptide coding sequence, or the nucleic acid can be cloned into one or more separate vectors for co-administration.

One approach to administration of nucleic acids is direct immunization with plasmid DNA, such as with a mammalian expression plasmid. The nucleotide sequence encoding a melioidosis-associated polypeptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, a melioidosis-associated polypeptide can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

A first recombinant virus, such as a poxvirus (for example, vaccine virus) encoding a melioidosis immunogenic polypeptide can be used in conjunction with a second recombinant virus which has incorporated into a viral genome or infectable portion thereof one or more genes or DNA sequences encoding B7-1, B7-2, or B7-1 and B7-2, wherein the composition is able to coinfect a host cell resulting in coexpression of the polypeptide and the B7-1, B7-2, or B7-1 and B7-2 encoding genes or DNA sequences (see U.S. Pat. Nos. 6,893,869, and 6,045,908, which are incorporated by reference herein).

When a viral vector is utilized, it is desirable to provide the recipient with a dosage of each recombinant virus in the composition in the range of from about $10^5$ to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant viral vector, carrying the nucleic acid sequence of one or more melioidosis polypeptides to be administered is based on the titer of virus particles. An exemplary range of the immunogen to be administered is $10^5$ to $10^{10}$ virus particles per mammal, such as a human.

In the embodiment where a combination of a first recombinant viral vector carrying a nucleic acid sequence of one or more melioidosis polypeptides and a second recombinant viral vector carrying the nucleic acid sequence of one or more immunostimulatory molecules is used, the mammal can be immunized with different ratios of the first and second recombinant viral vector. In one embodiment the ratio of the first vector to the second vector is about 1:1, or about 1:3, or about 1:5. Optimal ratios of the first vector to the second vector may easily be titered using the methods known in the art (see, for example, U.S. Pat. No. 6,893,869, incorporated herein by reference).

In one embodiment the recombinant viruses have been constructed to express cytokines (such as TNF-α, IL-6, GM-CSF, and IL-2), and co-stimulatory and accessory molecules (B7-1, B7-2) alone and in a variety of combinations. Simultaneous production of an immunostimulatory molecule and the melioidosis polypeptide enhances the generation of specific effectors. Without being bound by theory, dependent upon the specific immunostimulatory molecules, different mechanisms might be responsible for the enhanced immunogenicity: augmentation of help signal (IL-2), recruitment of professional APC (GM-CSF), increase in CTL frequency (IL-2), effect on antigen processing pathway and MHC expression (IFNγ and TNFα) and the like. For example, IL-2, IL-6, interferon, tumor necrosis factor, or a nucleic acid encoding these molecules, can be administered in conjunction with a melioidosis immunogenic polypeptide, or a nucleic acid encoding a melioidosis polypeptide. The co-expression of a melioidosis polypeptide together with at least one immunostimulatory molecule can be effective in an animal model to show anti-melioidosis effects.

In one embodiment, a nucleic acid encoding a melioidosis polypeptide is introduced directly into cells. For example, the nucleic acid can be loaded onto gold microspheres by standard methods and introduced into the skin by a device such as Bio-Rad's Helios™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 μg/kg to about 50 mg/kg, and typically are about 0.005 mg/kg to about 5 mg/kg (see, for example, U.S. Pat. No. 5,589,466).

In one specific, non-limiting example, a pharmaceutical composition for intravenous administration would include about 0.1 μg to 10 mg of immunogenic melioidosis polypeptide per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences,* $19^{th}$ Ed., Mack Publishing Company, Easton, Pa., 1995.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In another method, antigen presenting cells (APCs), such as dendritic cells, are pulsed or co-incubated with peptides comprising a melioidosis polypeptide in vitro. In one specific, non-limiting example, the antigen presenting cells can be autologous cells. A therapeutically effective amount of the antigen presenting cells can then be administered to a subject.

The melioidosis polypeptide can be delivered to the dendritic cells or to dendritic cell precursors via any method known in the art, including, but not limited to, pulsing dendritic cells directly with antigen, or utilizing a broad variety of antigen delivery vehicles, such as, for example, liposomes, or other vectors known to deliver antigen to cells. In one specific, non-limiting example an antigenic formulation includes about 0.1 μg to about 1,000 μg, or about 1 to about 100 μg of a selected melioidosis polypeptide. The melioidosis polypeptide can also be administered with agents that promote dendritic cell maturation. Specific, non-limiting examples of agents of use are interleukin-4 (IL-4) and granulocyte/macrophage colony stimulating factor (GM-CSF), or flt-3 ligand (flt-3L). The preparation can also contain buffers, excipients, and preservatives, amongst other ingredients.

In one embodiment, mature antigen presenting cells are generated to present the immunogenic melioidosis polypeptide. These dendritic cells are then administered alone (or in combination with another agent) to a subject with melioidosis.

In another embodiment, the mature dendritic cells are administered in conjunction with a composition known to those of ordinary skill in the art to treat melioidosis.

Alternatively, the APCs are used to sensitize CD8 cells, such as peripheral blood lymphocytes (PBLs). The PBLs can be from the same subject (autologous) that is to be treated. Alternatively, the PBLs can be heterologous. However, they should at least be MHC Class-I restricted to the HLA types the subject possesses. An effective amount of the sensitized cells are then administered to the subject.

Peripheral blood mononuclear cells (PBMCs) can be used as the responder cell source of CTL precursors. The appropriate antigen-presenting cells are incubated with peptide, after which the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the antigen from which the peptide sequence was derived, such as melioidosis.

The cells can be administered to a subject to inhibit one or more activities associated with melioidosis, including growth of cells expressing one or more melioidosis-associated molecules (such as those included in Table 2, including but not limited to LPS, CPS, BipC, flagellin, or GroEL).

In these applications, a therapeutically effective amount of activated antigen presenting cells, or activated lymphocytes, are administered to a subject suffering from a disease, in an amount sufficient to raise an immune response to melioidosis-associated molecules expressing cells. The resulting immune response is sufficient to slow the proliferation of such cells or to inhibit their growth, or to reduce a sign or a symptom of the disease.

In a supplemental method, any of these immunotherapies is augmented by administering a cytokine, such as interleukin (IL)-2, IL-3, IL-6, IL-10, IL-12, IL-15, GM-CSF, or interferons.

In a further method, any of these immunotherapies is augmented by administering an agent, such as, but not limited to, agents traditionally used to treat one or more systems associated with melioidosis.

i. Immunogenic Melioidosis Molecules Including Peptides

Exemplary immunogenic melioidosis molecules, including immunogenic melioidosis peptides, include those that are identified herein as being associated with melioidosis.

In one example, an immunogenic "melioidosis peptide" is a series of contiguous amino acid residues from a melioidosis-associated protein. In some examples, the immunogenic melioidosis peptides are about 7 amino acids in length to about 250 amino acids in length, for example, the may be at least 7, 8, 9, 10 or 11 residues in length, for example 10-30 residues, or 10-21 residues. The immunogenic melioidosis peptide can be incorporated into a fusion protein or the immunogenic melioidosis peptide can be incorporated into a polymer of repeating melioidosis peptides, or melioidosis peptides joined by non-melioidosis peptide linkers. The melioidosis peptides in some examples are about or no more than about 7, about 8, about 9, about 10, about 11, about 12, about 13, about 14, about 15, about 16, about 17, about 18, about 19, about 20, about 21, about 22, about 23, as about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200, about 201, about 202, about 203, about 204, about 205, about 206, about 207, about 208, about 209, about 210, about 211, about 212, about 213, about 214, about 215, about 216, about 217, about 218, about 219, about 220, about 221, about 222, about 223, about 224, about 225, about 226, about 227, about 228, about 229, about 230, about 231, about 232, about 233, about 234, about 235, about 236, about 237, about 238, about 239, about 240, about 241, about 242, about 243, about 244, about 245, about 246, about 247, about 248, about 249, or about 250 amino acids in length, for example about 8 to about 250, about 10 to about 150, about 12 to about 30, about 14 to about 20 amino acids in length or greater. In this context, it is understood that "about" refers to an integer quantity. In some examples, the melioidosis peptide is even greater than 250 amino acids in length, for example when part of a larger fusion protein.

In some examples, an immunogenic melioidosis peptide is an antigen set forth in Table 2. For example, an immunogenic melioidosis peptide is an antigen provided in Table 2, generally between 7 and 20 amino acids in length, such as about 8 to 15 residues in length. In some examples, an immunogenic melioidosis peptide is a series of contiguous amino acid residues from BipC, flagellin or GroEL, generally between 7 and 20 amino acids in length, such as about 8 to 15 residues in length. For example, a GroEL immunogenic peptide is a peptide with an amino acid sequence of C-TEVEVKEKKDRVDD (SEQ ID NO:1; starting at residue 385 of *Agrobacterium* sp. H13-3 GenBank Accession No. YP_004280298; which is hereby incorporated by reference as available on Mar. 14, 2011).

Consecutive repeats of exemplary immunogenic melioidosis peptides can be joined by a peptide linker between two and ten amino acids in length, such as about 2, about 3, about 4, about 5, about 6, about 7, about 8, about 9 or about 10 amino acids in length. Depending on such factors as the molecules to be linked, and the conditions in which the peptide is being administered (such as if the peptide is being used in a method of detection), the linker can vary in length and composition for optimizing such properties as flexibility, and stability. The linker is a peptide heterologous to the immunogenic melioidosis peptide. In some examples, a linker is peptide such as poly-lysine, poly-glutamine, poly-glycine, poly-proline or any combination combinations thereof. In some examples, the peptide linker can be designed to be either hydrophilic or hydrophobic in order to enhance the desired binding characteristics of the immunogenic melioidosis peptide The peptide linker and the individual units of the immunogenic melioidosis peptide can be encoded as a single fusion polypeptide such that the peptide linker and the individual units of the melioidosis peptide are joined by peptide bonds. In other embodiments, an immunogenic melioidosis peptide has an amino acid sequence at least 90% identical to a wild-type melioidosis-associated molecule (such as antigen listed in Table 1), for example a polypeptide that has at least about 91%, 92%, 93%, 94%, 95%, 96%, 97%, 98% or 99% sequence identity to a wild-type melioidosis-associated molecule (such as antigen listed in Table 2).

Using the genetic code, one of skill in the art can readily produce a nucleic acid sequence encoding a melioidosis-associated polypeptide (such as an antigen listed in Table 1).

The disclosed polypeptides disclosed herein can be chemically synthesized by standard methods, or can be produced recombinantly. An exemplary process for polypeptide production is described in Lu et al., *Federation of European Biochemical Societies Letters.* 429:31-35, 1998. They can also be isolated by methods including preparative chromatography and immunological separations.

A disclosed polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and LPS and/or CPS).

ii. Polynucleotides Encoding Immunogenic Melioidosis Peptides

Polynucleotides encoding the disclosed polypeptides disclosed herein are also provided. These polynucleotides include DNA, cDNA and RNA sequences which encode the polypeptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, Biochemistry, 3.sup.rd Edition, W.H. 5 Freeman and Co., NY).

A nucleic acid encoding a melioidosis polypeptide can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding a melioidosis protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding a melioidosis polypeptide include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides of the disclosure can be ribonucleotides, deoxyribonucleotides, or modified forms of either nucleotide. The term includes single and double forms of DNA.

In one embodiment, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, may inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUP1 promoters. Any of these promoters may be cloned into multicopy (2μ) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation.

The melioidosis peptides can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the melioidosis polypeptides disclosed herein. A number of viral vectors have been constructed, including polyoma, SV40 (Madzak et al., 1992, J. Gen. Virol., 73:15331536), adenovirus (Berkner, 1992, Cur. Top. Microbiol. Immunol., 158:39-6; Berliner et al., 1988, Bio Techniques, 6:616-629; Gorziglia et al., 1992, J. Virol., 66:4407-4412; Quantin et al., 1992, Proc. Nad. Acad. Sci. USA, 89:2581-2584; Rosenfeld et al., 1992, Cell, 68:143-155; Wilkinson et al., 1992, Nucl. Acids Res., 20:2233-2239; Stratford-Perricaudet et al., 1990, Hum. Gene Ther., 1:241-256), vaccinia virus (Mackett et al., 1992, Biotechnology, 24:495-499), adeno-associated virus (Muzyczka, 1992, Curr. Top. Microbiol. Immunol., 158:91-123; On et al., 1990, Gene, 89:279-282), herpes viruses including HSV and EBV (Margolskee, 1992, Curr. Top. Microbiol. Immunol., 158:67-90; Johnson et al., 1992, J. Virol., 66:29522965; Fink et al., 1992, Hum. Gene Ther. 3:11-19; Breakfield et al., 1987, Mol. Neurobiol., 1:337-371; Fresse et al., 1990, Biochem. Pharmacol., 40:2189-2199), Sindbis viruses (H. Herweijer et al., 1995, Human Gene Therapy 6:1161-1167; U.S. Pat. Nos. 5,091,309 and 5,2217,879), alphaviruses (S. Schlesinger, 1993, Trends Biotechnol. 11:18-22; I. Frolov et al., 1996, Proc. Natl. Acad. Sci. USA 93:11371-11377) and retroviruses of avian (Brandyopadhyay et al., 1984, Mol. Cell. Biol., 4:749-754; Petropouplos et al., 1992, J. Virol., 66:3391-3397), murine (Miller, 1992, Curr. Top. Microbiol. Immunol., 158:1-24; Miller et al., 1985, Mol. Cell. Biol., 5:431-437; Sorge et al., 1984, Mol. Cell. Biol., 4:1730-1737; Mann et al., 1985, J. Virol., 54:401-407), and human origin (Page et al., 1990, J. Virol., 64:5370-5276; Buchschalcher et al., 1992, J. Virol., 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

Thus, in one embodiment, the polynucleotide encoding a melioidosis polypeptide is included in a viral vector. Suitable vectors include retrovirus vectors, *orthopox* vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses useful in practicing the present invention include *orthopox*, suipox, avipox, and capripox virus. *Orthopox* include vaccinia, ectromelia, and raccoon pox. One example of an *orthopox* of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

In some cases, vaccinia viral vectors may elicit a strong antibody response. Thus, while numerous boosts with vaccinia vectors are possible, its repeated use may not be useful in certain instances. However, this sensitivity problem can be minimized by using pox from different genera for boosts. In one example, when the first or initial pox virus vector is vaccinia, the second and subsequent pox virus vectors are selected from the pox viruses from a different genus such as suipox, avipox, capripox or an *orthopox* immunogenically distinct from vaccinia.

The vaccinia virus genome is known in the art. It is composed of a HIND F13L region, TK region, and an HA region. Recombinant vaccinia virus has been used to incorporate an exogenous gene for expression of the exogenous gene product (see, for example, Perkus et al. *Science* 229:981-984, 1985; Kaufman et al. *Int. J. Cancer* 48:900-907, 1991; Moss *Science* 252:1662, 1991). A gene encoding an antigen of interest, such as an immunogenic melioidosis polypeptide, can be incorporated into the HIND F13L region or alternatively incorporated into the TK region of recombinant vaccinia virus vector (or other nonessential regions of the vaccinia virus genome). Baxby and Paoletti (*Vaccine* 10:8-9, 1992) disclose the construction and use as a vector, of the non-replicating poxvirus, including canarypox virus, fowlpox virus and other avian species. Sutter and Moss (*Proc. Nat'l. Acad. Sci. U.S.A.* 89:10847-10851, 1992) and Sutter et al. (Virology 1994) disclose the construction and use as a vector, the non-replicating recombinant Ankara virus (MVA, modified vaccinia Ankara) in the construction and use of a vector.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode a melioidosis polypeptide. The recombinant virus containing such a chimeric gene is effective at expressing the melioidosis polypeptide. In one example, the vaccine viral vector comprises (A) a segment comprised of (i) a first DNA sequence encoding a melioidosis polypeptide and (ii) a poxvirus promoter, wherein the poxvirus promoter is adjacent to and exerts transcriptional control over the DNA sequence encoding a melioidosis polypeptide; and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Poxviral vectors that encode a melioidosis polypeptide include at least one expression control element operationally linked to the nucleic acid sequence encoding the melioidosis polypeptide. The expression control elements are inserted in the poxviral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the melioidosis polypeptide in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in "Current Protocols in Molecular Biology," John Wiley and Sons, New York, N.Y.) and are commercially available.

Basic techniques for preparing recombinant DNA viruses containing a heterologous DNA sequence encoding the melioidosis polypeptide, are known in the art. Such techniques involve, for example, homologous recombination between the viral DNA sequences flanking the DNA sequence in a donor plasmid and homologous sequences present in the parental virus (Mackett et al., 1982, Proc. Natl. Acad. Sci. USA 79:7415-7419). In particular, recombinant viral vectors such as a poxviral vector can be used in delivering the gene. The vector can be constructed for example by steps known in the art, such as steps analogous to the methods for creating synthetic recombinants of the fowlpox virus described in U.S. Pat. No. 5,093,258, which is hereby incorporated by reference. Other techniques include using a unique restriction endonuclease site that is naturally present or artificially inserted in the parental viral vector to insert the heterologous DNA.

Generally, a DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding a melioidosis polypeptide located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into pox virus are described in WO91/19803, incorporated herein by reference.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono, di-, or multivalent (i.e., can contain one or more inserted foreign DNA sequences). The donor vector can contain an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, J. Virol. 62:1046; Falkner and Moss, 1988, J. Virol. 62:1849; Franke et al., 1985, Mol. Cell. Biol. 5:1918), as well as genes such as the *E. coli* lacZ gene, that permit identification of recombinant viral plaques by colorimetric assay (Panicali et al., 1986, Gene 47:193-199).

The DNA gene sequence to be inserted into the virus can be placed into a donor plasmid, such as an *E. coli* or a *Salmonella* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA that is the desired insertion region. With a parental pox viral vector, a pox promoter is used. The resulting plasmid construct is then amplified by growth within *E. coli* bacteria and isolated. Next, the isolated plasmid containing the DNA gene sequence to be inserted is transfected into a cell culture, for example chick embryo fibroblasts, along with the parental virus, for example poxvirus. Recombination between homologous pox DNA in the plasmid and the viral genome respectively results in a recombinant poxvirus modified by the presence of the promoter-gene construct in its genome, at a site that does not affect virus viability.

As noted above, the DNA sequence is inserted into a region (insertion region) in the virus that does not affect virus viability of the resultant recombinant virus. One of skill in the art can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. The TK gene has been found in all pox virus genomes examined, including leporipoxvirus (Upton et al., 1986, J. Virology 60:920); shope fibromavirus; capripoxvirus (Gershon et al., 1989, J. Gen. Virol. 70:525) Kenya sheep-1; orthopoxvirus (Weir et al., 1983, J. Virol. 46:530) vaccinia (Esposito et al., 1984, Virology 135:561); monkeypox and variola virus (Hruby et al., 1983, PNAS 80:3411) vaccinia (Kilpatrick et al., 1985, Virology 143:399); Yaba monkey tumor virus; avipoxvirus (Binns et al., 1988, J. Gen. Virol. 69:1275); fowipox; (Boyle et al., 1987, Virology 156:355); fowlpox (Schnitzlein et al., 1988, J. Virological Methods 20:341); fowlpox, quailpox; entomopox (Lytvyn et al., 1992, J. Gen. Virol. 73:3235-3240). In vaccinia, in addition to the TK region, other insertion regions include, for example, the Hind111 M fragment. In fowlpox, in addition to the TK region, other insertion regions include, for example, the BamHI J fragment (Jenkins et al., 1991, AIDS Research and Human Retroviruses 7:991-998) the ECORI-HindIII fragment, EcoRV-HindIII fragment, BamHI fragment and the HindIII fragment set forth in EPO Application No. 0 308220 A1 (see also Calvert et al., 1993, J. Virol. 67:3069-3076; Taylor et al., 1988, Vaccine 6:497-503; Spehner et al., 1990; Boursnell et al., 1990, J. Gen. Virol. 71:621-628).

In swinepox, insertion sites include the thymidine kinase gene region. In addition to the requirement that the gene be inserted into an insertion region, successful expression of the inserted gene by the modified poxvirus requires the presence of a promoter operably linked to the desired gene. Generally, the promoter is placed so that it is located upstream from the gene to be expressed. Promoters are well known in the art and can readily be selected depending on the host and the cell type you wish to target. In one example, in poxviruses, pox viral promoters are used, such as the vaccinia 7.5K, 40K or fowlpox promoters such as FPV CIA. Enhancer elements can also be used in combination to increase the level of expression. Furthermore, inducible promoters can be utilized.

Homologous recombination between donor plasmid DNA and viral DNA in an infected cell can result in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (see U.S. Pat. No. 4,603,112 and PCT Publication No. WO 89/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK- and can be selected on this basis (Mackett et al., 1982, Proc. Natl. Acad. Sci. USA 79:7415). Alternatively, co-integration of a gene encoding a marker or indicator gene with the foreign gene(s) of interest, as described above, can be used to identify recombinant progeny. One specific non-limiting example of an indicator gene is the *E. coli* lacZ gene. Recombinant viruses expressing beta-galactosidase can be selected using a chromogenic substrate for the enzyme (Panicali et al., 1986, Gene 47:193). Once a recombinant virus has been identified, a variety of well-known methods can be used to assay the expression of the melioidosis sequence encoded by the inserted DNA fragment. These methods include black plaque assay (an in situ enzyme immunoassay performed on viral plaques), Western blot analysis, radioimmunoprecipitation (RIPA), and enzyme immunoassay (EIA).

This disclosure encompasses a recombinant virus comprising more than one antigen of interest for the purpose of having a multivalent vaccine. For example, the recombinant virus may comprise the virus genome or portions thereof, the nucleic acid sequence encoding a melioidosis polypeptide and a nucleic acid sequence encoding a hepatitis B surface antigen.

In one embodiment, a composition is provided that includes a recombinant virus comprising a vaccinia virus genome or portions thereof, the nucleic acid sequence encoding a melioidosis polypeptide and a recombinant virus comprising the nucleic acid sequence encoding the immunostimulatory molecule, B 7.1 alone or in combination with the nucleic acid sequence encoding the immunostimulatory molecule, B7-2, or a recombinant virus containing both the genes for a melioidosis antigen and an immunostimulatory molecule. This disclosure also encompasses a recombinant virus comprising the melioidosis polypeptide that is administered with a second recombinant virus comprising the virus genome or portion thereof, and one or more nucleic acid sequences encoding one or more B7 molecules, such as a recombinant vaccinia virus expressing B7-1 and/or B7-2.

Significant amplification of the immune response against a given antigen generally does not occur without co-stimulation (June et al. (*Immunology Today* 15:321-331, 1994); Chen et al. (*Immunology Today* 14:483-486); Townsend et al. (*Science* 259:368-370)). Freeman et al. (*J. Immunol.* 143:2714-2722, 1989) report cloning and sequencing of B7-1 gene. Azuma et al. Nature 366:76-79, 1993) report cloning and sequencing B7-2 gene. Thus, in one embodiment the B7-1 gene or the B7-2 genes are administered in conjunction with the melioidosis polypeptide. The insertion of nucleic acids encoding B7-1 and B7-2 into vaccinia virus has been disclosed (see for example, U.S. Pat. No. 6,893,869, incorporated herein by reference; this U.S. Patent also discloses the use of a nucleic acid encoding IL-2 in a vaccinia virus). Several vectors including IL-2, B7-1 and B7-2 have been deposited with the American Type Culture Collection (ATCC) on Oct. 3, 1994 under the terms of the Budapest Treaty (for example, rV-CEA/$_{n}$IL-2 (ATCC Designation VR 2480), rV-$_{m}$B7-2 (ATCC Designation VR 2482); and rV-$_{m}$B7-1 (ATCC Designation VR 2483)).

DNA sequences encoding a melioidosis polypeptide can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding a melioidosis polypeptide can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods Methods in Enzymology 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding a melioidosis polypeptide, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982).

VI. Methods for Treating Melioidosis

Methods are disclosed for treating a subject having melioidosis. In some embodiments, these methods include inducing an immune response to melioidosis and/or using an inhibitory nucleic acid, such as a siRNA or antisense molecule, to decrease melioidosis-associated molecule expression in order to treat melioidosis. In some examples, the methods include treating a subject with a disease or condition associated with *B. mallei, B. pseudomallei, B. thailandensis* or a combination thereof. In some examples, the disclosed method is used for treating a subject with acute melioidosis. In some examples, the method is used for treating a subject with chronic melioidosis.

The methods can include selecting a subject in need of treatment, such as a subject that expresses one or more melioidosis-associated antigens (such as those provided in Table 2) or exhibits one or more signs or symptoms known to one of skill in the art to be associated with melioidosis. In one example, the method includes administering a therapeutically effective amount of a specific binding agent that preferentially binds to a melioidosis-associated molecule. The specific binding agent can be an inhibitor such as a siRNA or an antisense molecule that specifically binds a mRNA which translates into a protein associated with melioidosis. Inhibition of melioidosis does not require 100% inhibition, but can include at least a reduction if not a complete inhibition of cell growth or differentiation associated with a specific pathological condition. Treatment of melioidosis by inhibiting or reducing expression of one or more melioidosis molecules can include delaying the development of melioidosis in a subject. Treatment of melioidosis also includes reducing signs or symptoms associated with melioidosis. In some examples, a decrease or slowing melioidosis progression is an alteration of at least 10%, at least 20%, at least 50%, or at least 75%. In some examples, treatment using the methods disclosed herein is used to prevent reoccurrence of melioidosis or the severity of melioidosis systems if it does reoccur. Treatment can also result in modulation, such as down-regulation, of melioidosis markers (such as one or more antigens listed in Table 2).

Specific binding agents are agents that bind with higher affinity to a melioidosis-associated molecule, than to other molecules. For example, a specific binding agent can be one that binds with high affinity to a melioidosis-associated molecule but does not substantially bind to another gene or gene product. For example, the specific binding agent interferes with gene expression (transcription, processing, translation, post-translational modification), such as, by interfering with a melioidosis-associated mRNA and blocking translation into protein.

A reduction in the expression of a melioidosis-associated protein in a target cell may be obtained by introducing into cells an antisense or other suppressive construct based on the melioidosis-associated molecule coding sequence. For antisense suppression, a nucleotide sequence from a melioidosis-associated molecule encoding sequence, e.g. all or a portion of the melioidosis-associated cDNA or gene, is arranged in reverse orientation relative to the promoter sequence in the transformation vector.

The introduced sequence need not be the full length the gene which encodes the melioidosis-associated protein, and need not be exactly homologous to the equivalent sequence found in the cell type to be transformed. Thus, portions or fragments of a nucleic acid encoding a melioidosis-associated protein could also be used to knock out or suppress expression. Generally, however, where the introduced sequence is of shorter length, a higher degree of identity to the native melioidosis-associated molecule sequence will be needed for effective antisense suppression. The introduced antisense sequence in the vector may be at least 15 nucleotides in length, and improved antisense suppression typically will be observed as the length of the antisense sequence increases. The length of the antisense sequence in the vector advantageously may be greater than 100 nucleotides, and can be up to about the full length of the one or more melioidosis-associated cDNA or gene. For suppression of the melioidosis gene itself, transcription of an antisense construct results in the production of RNA molecules that are the reverse complement of mRNA molecules transcribed from the endogenous melioidosis-associated gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA. Expression of a melioidosis-associated molecule can also be reduced using small inhibitory RNAs, for instance using techniques similar to those described previously (see, e.g., Tuschl et al., *Genes Dev* 13, 3191-3197, 1999; Caplen et al., *Proc. Nat'l Acad. Sci. U.S.A.* 98, 9742-9747, 2001; and Elbashir et al., *Nature* 411, 494-498, 2001). Methods of making siRNA that can be used clinically are known in the art. Exemplary siRNAs are commercially available from several sources, such as Sigma Aldrich and Dharmacon, and therapeutic siRNAs can readily be produced using methods known in the art.

Suppression of endogenous melioidosis-associated molecule expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

In certain examples, expression vectors are employed to express the inhibitor nucleic acid, such as the antisense, ribozyme or siRNA molecule (see above for additional information on vectors and expression systems). For example, an expression vector can include a nucleic acid sequence encoding the antisense, ribozyme or siRNA molecule. In a particular example, the vector contains a sequence(s) encoding both strands of a siRNA molecule comprising a duplex. In another example, the vector also contains sequence(s) encoding a single nucleic acid molecule that is self-complementary and thus forms a siRNA molecule. Non-limiting examples of such expression vectors are described in Paul et al., *Nature Biotechnology* 19:505, 2002; Miyagishi and Taira, *Nature Biotechnology* 19:497, 2002; Lee et al., *Nature Biotechnology* 19:500, 2002; and Novina et al., *Nature Medicine*, online publication Jun. 3, 2003, and additional vectors are described herein.

In other examples, inhibitory nucleic acids, such as siRNA molecules include a delivery vehicle, including inter alia liposomes, for administration to a subject, carriers and diluents and their salts, and can be present in pharmaceutical compositions. Nucleic acid molecules can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722, see also the additional methods described above).

Alternatively, the nucleic acid/vehicle combination can be locally delivered by direct injection or by use of an infusion pump. Direct injection of the nucleic acid molecules of the disclosure, whether subcutaneous, intramuscular, or intradermal, can take place using standard needle and syringe methodologies, or by needle-free technologies such as those described by Barry et al., International PCT Publication No. WO 99/31262. Other delivery routes include, but are not limited to, oral delivery (such as in tablet or pill form), intrathecal or intraperitoneal delivery (see below). For example, intraperitoneal delivery can take place by injecting the treatment into the peritoneal cavity of the subject. More detailed descriptions of nucleic acid delivery and administration are provided in Sullivan et al., PCT WO 94/02595, Draper et al., PCT Publication No. WO93/23569, Beigelman et al., PCT WO99/05094, and Klimuk et al., PCT Publication No. WO 99/04819, all of which are incorporated by reference herein.

Alternatively, certain siRNA molecules can be expressed within cells from eukaryotic promoters. Those skilled in the art will recognize that any nucleic acid can be expressed in eukaryotic cells using the appropriate DNA/RNA vector (see above). The activity of such nucleic acids can be augmented by their release from the primary transcript by an enzymatic nucleic acid (Draper et al., PCT Publication No. WO 93/23569, and Sullivan et al., PCT Publication No. WO 94/02595).

In other examples, siRNA molecules can be expressed from transcription units (see for example, Couture et al., 1996, TIG 12:510) inserted into DNA or RNA vectors. The recombinant vectors can be DNA plasmids or viral vectors. siRNA expressing viral vectors can be constructed based on, for example, but not limited to, adeno-associated virus, retrovirus, adenovirus, lentivirus or alphavirus. In another example, pol III based constructs are used to express nucleic acid molecules of the invention (see for example, Thompson, U.S. Pat. Nos. 5,902,880 and 6,146,886 and others described above).

The recombinant vectors capable of expressing the siRNA molecules can be delivered as described above, and persist in target cells. Alternatively, viral vectors can be used that provide for transient expression of nucleic acid molecules. Such vectors can be repeatedly administered as necessary. Once expressed, the siRNA molecule interacts with the target mRNA and generates an RNAi response. Delivery of siRNA molecule expressing vectors can be systemic, such as by intravenous or intramuscular administration, by administration to target cells explanted from a subject followed by reintroduction into the subject, or by any other means that would allow for introduction into the desired target cell.

The disclosure is illustrated by the following non-limiting Examples.

EXAMPLES

Example 1

Passive Protection in a Murine Model of Pulmonary Melioidosis and Direct Identification of B. pseudomallei* Antigens in Human Urine with Lipopolysaccharide and Capsular Polysaccharide Specific Monoclonal Antibodies This example demonstrates passive protection in a murine model of pulmonary melioidosis and direct identification of *B. pseudomallei* antigens in human urine with lipopolysaccharide and capsular polysaccharide specific monoclonal antibodies.

Material and Methods

Immunization of Mice and Production of LPS, CPS and EPS mAbs. Production of mAbs 4C7 and 3C5 began with immunization of BALB/c mice with heat-inactivated *B. pseudomallei* (strain 1026b). An intraperitoneal injection of $2\times10^8$ bacteria was administered every two weeks for an eight-week period. An ELISA, with heat-inactivated strain 1026b in the solid phase, was used to assess antibody levels to *B. pseudomallei*. Three days prior to harvest of spleens, one final intraperitoneal immunization of $2\times10^8$ bacteria was administered. Hybridoma cells were produced. Western blot analysis was done to identify hybridoma cell lines that were producing anti-LPS (ladder pattern) and anti-CPS (high molecular weight, proteinase K insensitive) mAbs. Hybridoma cell lines were grown in Integra CL 1000 culture flasks (Integra Biosciences) and mAbs were purified by affinity chromatography over a protein-A column. EPS mAbs were produced by immunization of mice with cells of *Burkholderia cepacia* (strain BTS-13) that produces an EPS identical to that of *B. pseudomallei*. The EPS mAbs were reactive with whole cells of *B. pseudomallei* by ELISA and immunofluorescence.

Western Blot Analysis. A standard Western blot procedure using semi-dry blotting (mAb 4C7) and tank blotting (mAb 3C5) was used in this study. Briefly, $8\times10^6$ bacterial cells were suspended in Laemmli Sample Buffer (Sigma Aldrich, St. Louis, Mo. Cat #53401-10VL) and incubated at 100 C. for 10 min. If required, one volume of a proteinase K solution (3.3 mg in 1 mL Laemmli Sample Buffer) was added and the sample was incubated at 60 C. for 1 hour. In addition to *B. pseudomallei* lysates, 20 μL of urine from melioidosis patients (or control urine) was suspended in Laemmli Sample Buffer for Western blot analysis. Samples were run on either a 10-20% SDS gradient gel or a 10% SDS gel followed by transfer onto a PVDF membrane. mAbs 4C7 (0.73 mg/ml) and 3C5 (0.89 mg/ml) were used at a dilution of 1:10,000. Goat anti-mouse IgG-HRP (Southern Biotech) was used at a 1:10,000 dilution and signal was detected with a chemiluminescent substrate (Pierce Scientific).

Immunofluorescence Analysis. A suspension heat-inactivated bacteria was smeared onto a microscope slide and allowed to dry. Cells were fixed with methanol and the slide was washed by repeated dipping in water. mAb was applied directly to the slide and incubated for 90 min at room temp. After rinsing by dipping in fresh water, mAb binding was detected using an Alexa Fluor 555-labeled goat anti-mouse IgG (Invitrogen, Carlsbad, Calif.) diluted 1:1000 in PBS and incubated for 1 hr at room temp. The slide was then rinsed in fresh water, allowed to dry, and a coverslip was mounted with Vectashield (Vector Laboratories, Burlingame, Calif.). Fluorescence was evaluated using a Nikon Eclipse E800 epifluorescence microscope fitted with a Nikon C1 confocal microscopy attachment (Nikon Instruments, Inc.).

Antigen-Capture Immunoassay for CPS and LPS. Microtiter plates were coated overnight with either mAb 3C5 (CPS) or 4C7 (LPS) at 1 μg/ml in PBS, washed with PBS-Tween (PBS containing 0.5% Tween 20), and blocked by incubation for an additional 90 min with PBS-Tween. Serial dilutions of serum, urine, and *B. pseudomallei* crude extract were prepared in PBS-Tween and incubated for 90 min at room temperature with the mAb-coated wells. The wells were washed with PBS-Tween, incubated for 90 minutes with horseradish peroxidase-labeled (Pierce) mAb 3C5 or 4C7, washed, and incubated with tetramethylbenzidine substrate (Kirkegaard & Perry Laboratories).

Murine Model of Pulmonary Melioidosis. Briefly, Balb/c mice were injected with 1 mg of mAb (3C5, 4C7, or control mAb) by the intraperitoneal route 18 hr prior to challenge. A vial of frozen *Burkholderia pseudomallei* 1026b was thawed and diluted in PBS to a concentration of approximately 5000 CFU/25 μl, which represents approximately 15 $LD_{50}$ (lower doses lead to more chronic disease with disseminated abscess formation). Following challenge, the inoculum was back-titrated on agar plates to confirm delivered dose. Mice were anesthetized, held vertically, and 25 μl of the inoculum were released into the nares for inhalation. The mice were then wrapped in a paper towel and allowed to recover. Mice were weighed prior to inoculation, daily for 10 days, then twice weekly until 4 weeks post-challenge. Using this challenge model, control mice became debilitated and required euthanasia 3-4 days post-challenge.

Results mAbs 3C5 and 4C7 were produced by immunizing BALB/c mice with heat-inactivated *B. pseudomallei* strain 1026b. The mAbs were labeled with horseradish peroxidase (HRP) and used to probe *B. pseudomallei* whole cell lysates by Western blot analysis. As shown in FIG. 1 mAb 3C5 is reactive to a high molecular weight, proteinase K insensitive *B. pseudomallei* antigen (lanes 1 and 2). mAb 4C7 is reactive with multiple proteinase-K insensitive antigens (lanes 5 and 6); this pattern is characteristic of *B. pseudomallei* LPS laddering {Anuntagool, 2000 #799; Anuntagool, 1998 #994; Anuntagool, 2002 #751; Zou, 2008 #116}. Reactivity of the mAbs with proteinase K treated whole cell lysates provides evidence that the antigens are polysaccharides. mAb 3C5 was not reactive with a whole cell lysate produced from a capsular polysaccharide (CPS) mutant of *B. pseudomallei* strain SR1015 while mAb 4C7 was reactive (lanes 3 and 7, respectively). These studies demonstrate mAb 3C5 binds to CPS I and mAb 4C7 binds to LPS. Both mAbs 3C5 and 4C7 are of the IgG3 subclass, this was determined by ELISA utilizing subclass specific anti-IgG secondary antibodies.

It was next determined if mAbs 3C5 and 4C7 were reactive with other closely related *Burkholderia* species. mAb 4C7 produced a ladder pattern (that was identical to *B. pseudomallei*) when used to probe *B. thailandensis* and *B. mallei* (FIG. 2, lanes 1-3). The LPS O-antigen structures of *B. pseudomallei* and *B. thailandensis* have been shown to be identical. The O-antigen of *B. mallei* is slightly different; it does not produce acetyl modifications at the 0-4 position of L-6dTalp. Other groups have produced mAbs to *B. pseudomallei* LPS; most of these mAbs are not reactive to both *B. mallei* and *B. thailandensis*. mAb 3C5 was able to bind to *B. mallei* (although at a slightly lower molecular weight) and was unable to bind to *B. thailandensis* (FIG. 2, lanes 1-3). Both mAbs were unreactive by Western blot with nine representative species from the *Burkholderia cepacia* complex and seven other bacteria outside of the *Burkholderia* genus (Table 1). IFA results are illustrated in FIG. 3.

Both mAbs were used to develop an antigen-capture ELISA in order to identify CPS I and LPS antigens in solution. Either mAbs 3C5 or 4C7 were used in the capture (solid) phase of a 96-well ELISA plate. Following a blocking step, a crude *B. pseudomallei* soluble polysaccharide extract was serially diluted across the plate wells. The concentration the polysaccharides were determined. The wells were then washed and HRP-labeled mAb 3C5 or 4C7 was used in the indicator (detection) phase. The graphs in FIG. 4 shows mAb 3C5 was able to detect CPS I in the *B. pseudomallei* extract at a level of 16-32 ng/ml (OD value of 0.5). mAb 4C7 was able to detect LPS to a level of 250 ng/ml. Both of the antigens were detected by the capture ELISA.

Next, mAbs 3C5 and 4C7 were used to detect antigen in the serum and urine of melioidosis patients from Thailand. Twenty serum samples and 27 urine samples from confirmed melioidosis cases were acquired. It was determined that ten of the serum samples and 10 of the urine samples contained *B. pseudomallei*. The amount of bacteria in the urine ranged from an estimated 1000 to greater than 100,000 colony forming units/ml (cfu/ml). The amount of bacteria in the ten serum samples was unknown, however, recent studies have determined that positive serum samples from melioidosis patients only contain a median level of 1.1 cfu/ml. The same two studies also determined that positive urine samples contained roughly $1\times10^4$ cfu/ml. mAb 4C7 was not able to detect LPS in these patient samples by Western blot or capture ELISA. Western blot and ELISA showed strong reactivity of mAb 3C5 to CPSI when urine samples containing over $1\times10^5$ cfu/ml were used (FIG. 5). Weak reactivity was seen in a urine sample that contained an estimated $7.5\times10^4$ cfu/ml (FIG. 5, sample 1). mAb 3C5 was unable to detect CPSI in urine samples that did not contain bacteria. All of the samples tested were passed through a 0.22 μm filter; therefore, no whole cells were present in the samples.

The mAbs were tested for their ability to passively protect in a murine model of pulmonary melioidosis. BALB/c mice were challenged with 5000 cfu of *B. pseudomallei* followed 18 h later by an intraperitoneal injection of 1 mg of mAb 3C5 or 4C7 or both mAbs in combination (1 mg each). mAb 3C5 was able to protect most of the infected mice (6/7 survived) and mAb 4C7 was able to protect half (4/8 survived) of the mice tested (FIG. 6A). Mice that received both mAb all survived the challenge (6/6). Control mice, injected with 1 mg of an IgG3 mAb specific for the capsule of *Bacillus anthracis*, were euthanized at day 3 due to their poor condition. Spleen CFU and abscess formation was also determined in the mice that survived the pulmonary challenge. Most of the mice that received mAb 4C7 had a positive spleen CFU (3/4 mice) and abscess formation (3/4 mice). Most of the mice that received mAb 3C5 had a positive spleen CFU (4/6), however, these mice did not appear to develop abscsesses (0/6). Mice that received both mAbs in combination did not develop spleen CFU nor did they appear to develop abscesses. In addition, as illustrated in FIG. 6A (left panel), the administration of the combination of antibodies resulted in complete protective. The effect of varying the concentration of the two antibodies was determined over the course of 42 days. As illustrated in FIG. 6C, when the CPS mAb coated latex beads are combined with whole *B. pseudomallei* cells, agglutination occurs.

Discussion

The goal of this study was to determine the therapeutic and diagnostic potential of two mAbs specific for the CPS (mAb 3C5) and LPS (mAb 4C7) of *B. pseudomallei*. The present studies demonstrated the specificity of mAb 4C7 and mAb 3C5 and suggest that these antibodies have both therapeutic and diagnostic uses. Four *B. pseudomallei* capsule structures have been described and the exopolysaccharide (EPS) and the CPS have been determined to be high molecular weight polysaccharide antigens. There is much ambiguity relating to these two polysaccharides; many mAbs have been described to be specific to "high molecular weight polysaccharides" or "capsular polysaccharides" in general. For this reason a *B. pseudomallei* CPS mutant strain SR1015 was evaluated that was generated from the parental strain 1026b by transposon mutagenesis. mAb 3C5 was unable to bind to SR1015 lysate suggesting that the mAb was most likely specific to the CPS. Additional evidence that mAb 3C5 is reactive with the CPS relate to its specificity to other *Burkholderia* strains. mAb 3C5 was not reactive with *B. thailandensis* but was reactive with *B. mallei* by Western blot. The *B. pseudomallei* capsular gene cluster is present in *B. mallei*, however this cluster is truncated in *B. thailandensis*.

TABLE 1

| Bacterium | Strain(s) | mAb 3C5 CPS immunoreactivity* | mAb 4C7 LPS immunoreactivity |
|---|---|---|---|
| B. mallei | BEI resources | +++ | +++++ |
| B. pseudomallei | 1026b | +++ | +++ |
| B. thailandensis | E264 | − | +++ |
| B. multivorans | HI2229 | − | − |
| B. vietnamiensis | PC259 | − | − |
| B. dolosa | AU0654 | − | − |
| B. ambifaria | HI2468 | − | − |
| B. cenocepacia | HI2718 | − | − |
| B. anthina | AU1293 | − | − |
| B. stabilis | HI2210 | − | − |
| B. pyrrocinia | BC11 | − | − |
| B. cepacia | BTS13 | − | − |
| Pseudomonas aeruginosa | ATCC 27853 | − | − |
| Streptococcus pneumoniae | ATCC 10015 | − | − |
| Klebsiella pnuemoniae | ATCC 13883 | − | − |
| Staphylococcus aureus | ATCC 25923 | − | − |
| Enterobacter cloacae | ATCC 23355 | − | − |
| Providencia stuartii | ATCC 33672 | − | − |
| Escherichia coli | ATCC 25922 | − | − |

Example 2

In Vivo Microbial Antigen Discovery Method

This example provides an in vivo Microbial Antigen Discovery (InMAD) which is a method that allows the identification of microbial antigens that are shed into body fluids during infection.

Figure 7:
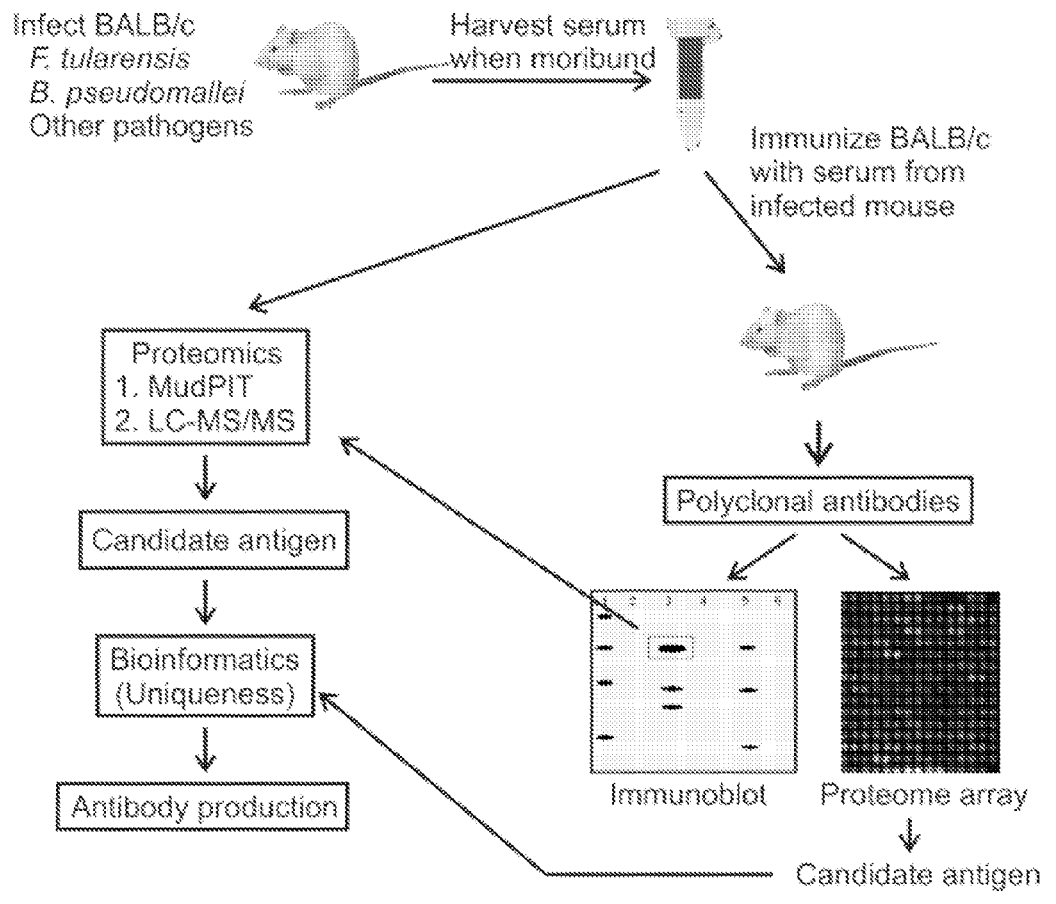

FIG. 7 provides a schematic of InMAD. InMAD was demonstrated to be capable of identifying antigens shed in vivo from *Francisella tularensis* and *B. pseudomallei*. The hypothesis was that serum or urine from BALB/c mice infected with a microbial pathogen would contain precisely those antigens that would be targets for immunoassay. If so, immunization of syngeneic BALB/c mice with filtered serum from an infected BALB/c mouse would produce an immune response to microbial antigens contained in the serum. Alternatively, serum or urine can be directly analyzed by mass spectrometry to identify microbial antigens.

Figure 8:
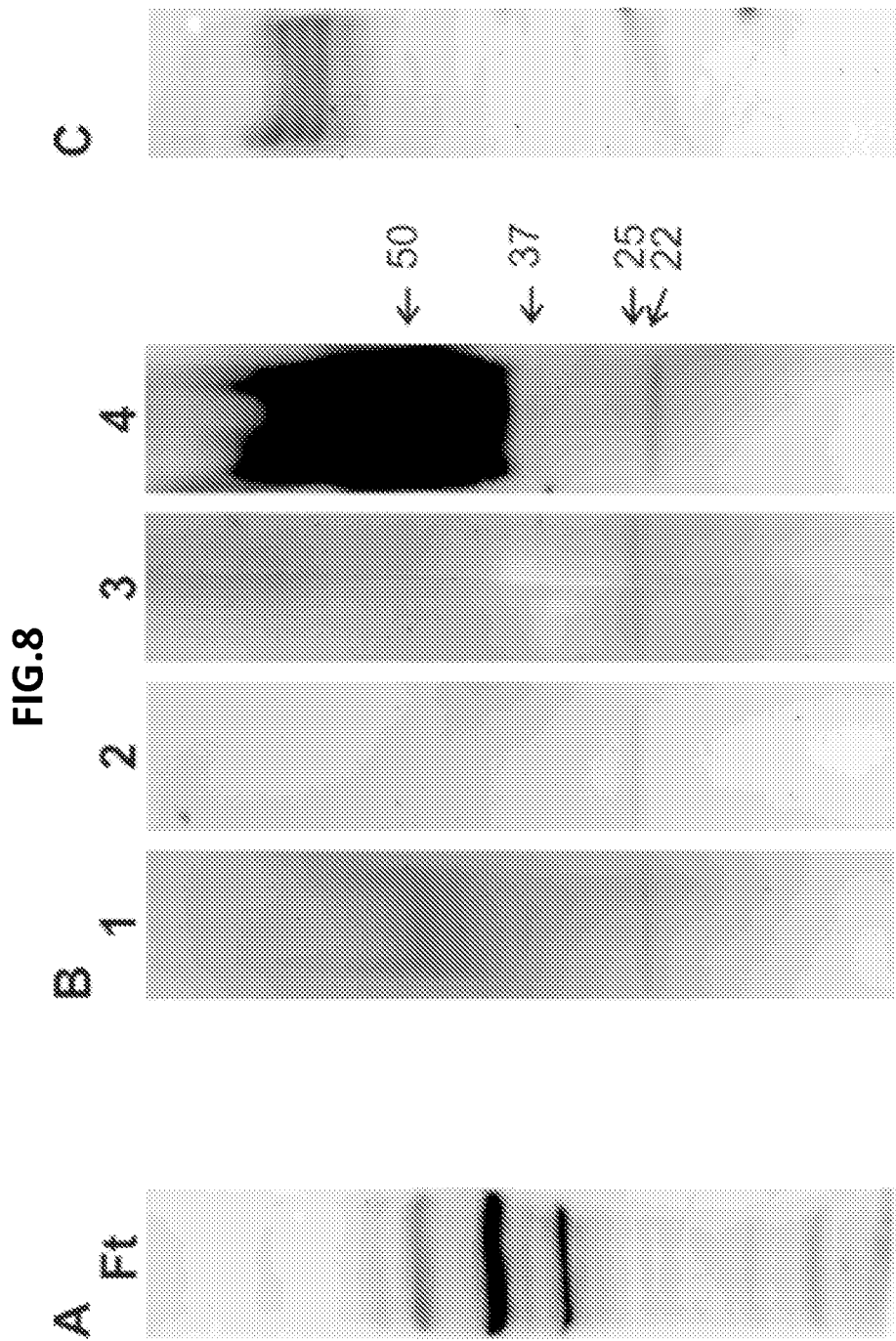

One study used serum from BALB/c mice that were infected with *F. tularensis*. The serum was filtered to remove any intact bacteria and used to immunize naïve BALB/c mice to raise antibodies to microbial molecules found in the serum. Serum from the immunized mice was used in three ways. First, the serum was used to probe a lysate of *F. tularensis* bacteria by immunoblot. At least six *F. tularensis* proteins were immunoreactive with antibodies in the serum (FIG. 8, Panel A). Second, the serum was used to probe a *F. tularensis* proteome array. Twelve proteins in the array were reactive with the immune serum. Finally, in a complementary approach, filtered serum from infected mice was subject to direct analysis by LC/LC-MS/MS and SDS-PAGE/LC-MS/MS. Results were queried against the *F. tularensis* database. Nine *F. tularensis* proteins were identified. Similar studies can be performed to identify *B. pseudomallei* antigens shed into serum of infected mice. Serum from *B. pseudomallei*-infected BALB/c mice was provided. The serum was filtered, and BALB/c mice were immunized with the serum. Probing of immunoblots prepared from whole cell lysates of *B. pseudomallei* with the immune serum (FIG. 8, Panel B) showed mouse-to-mouse variability in antibody production and in recognition of different antigens. At least three proteins were recognized (37, 25 and 22 kDa) as well as a diffuse area of staining that was most likely a polysaccharide (mouse #4). If the gels were prepared to optimize LPS laddering, the blot produced a banding pattern that is highly suggestive of LPS (FIG. 8, Panel C). Finally, proteomic analysis by LC/LC-MS/MS identified at least three *B. pseudomallei* proteins in the filtered serum. These studies demonstrate that the effective of InMAD technology for antigen discovery using both immunization of naïve mice with serum from infected mice to produce antibodies reactive with bacterial antigens in a proteome array and by direct proteomic analysis.

Example 3

Lateral Flow Immunoassay

This example provides an example of a lateral flow immunoassay. Although the assay was for early diagnosis of anthrax, it is contemplated that a similar approach can be used to produce a POC immunoassay for diagnosis of melioidosis.

To determine if a lateral flow immunoassay could be produced to diagnose melioidosis, first an immunoassay for diagnosis of anthrax was produced. The lateral flow immunoassay for early diagnosis of anthrax targeted the polyglutamic acid (PGA) capsule. PGA mAbs were generated and used to demonstrate that the antigen is shed into serum in murine, rabbit and non-human primate models of anthrax. PGA was detected by immunoassay at or before the time that the blood culture became positive. PGA is also shed in large amounts into urine during infection, raising the possibility for non-invasive sample collection. The immunoassay was then migrated from an ELISA format to a lateral flow format that is suitable for POC use. These studies not only demonstrated the ability to produce a functioning lateral flow immunoassay, but also suggest that a similar approach can be used to produce a POC immunoassay for diagnosis of melioidosis.

Example 4

Lateral Flow Immunoassay

This example provides an example of a lateral flow immunoassay for detection of CPS and LPS which can be used for the diagnosis of melioidosis. Although the assay was for detection of CPS and LPS, it is contemplated that a similar approach can be used to produce a point-of-care (POC) immunoassay with other melioidosis-associated molecules, including GroEL, BipC and/or flagellin for the diagnosis of melioidosis.

The lateral flow immunoassay for detection of CPS and LPS was produced as illustrated in FIG. 9B. CPS and LPS mAbs were generated. CPS and LPS were detected by the lateral flow immunoassay. The assay included various negative controls (such as Leishmaniasis serum and Chagas serum), dilutions of *B. pseudomallei* (Bp) and *B. thailandensis* (Bt) whole cell lysates, and normal human serum (NHS). CPS and LPS antigen were captured by CPS and LPS on the test lines. These studies not only demonstrated the ability to produce a functioning lateral flow immunoassay for detection of CPS and LPS, but also suggest that a similar approach can be used to produce a POC immunoassay for diagnosis of melioidosis with other melioidosis-associated molecules including GroEL, BipC and/or flagellin.

Example 5

Identification of Circulating Bacterial Antigens by In Vivo Bacterial Antigens by In Vivo Microbial Antigen Discovery (InMAD)

This example illustrates identification of circulating bacterial antigens by in vivo bacterial antigens by in vivo antigen discover.

Diagnosis of melioidosis can be difficult because the symptoms of melioidosis mimic other common infections. Isolation of B. pseudomallei from cultures of patient samples remains the "gold standard" for diagnosis. However, detection of B. pseudomallei is difficult due to limited experience of personnel and a lack of validated diagnostic reagents. Further, the concentration of B. pseudomallei antigen in serum is quite low. Moreover, speed to diagnosis is important since B. pseudomallei are resistant to many antibiotics given to treat common infections. The studies described below identify bacterial antigens that can be used to indicate melioidosis.

FIG. 7 illustrates the InMAD strategy used for identifying secreted/shed *B. pseudomallei* antigens. Balb/c mice were infected with *B. pseudomallei*, and InMAD serum was harvested when mice became moribund. The InMAD serum was filtered to remove whole bacteria, and secreted/shed bacterial antigens in the sample passed through the filter. Syngeneic mice were then immunized with the InMAD serum combined with adjuvant. InMAD immune serum was harvested from the immunized mice and used to probe bacterial cell lysates by 2-D Western blot or a bacterial proteome array. Reactive proteins were identified by mass spectrometry and are provided in Table 2 and FIG. 10. Polysaccharide antigens LPS and CPS were also detected (see FIG. 11).

TABLE 2

*B. pseudomallei* protein antigens reactive with InMAD immune serum by 2-D Western blot.

| Locus tag | Protein name | Localization | Protein score[a] |
|---|---|---|---|
| BPSS0477 | Chaperonin GroEL | Cytoplasmic | 1200 |
| BPSL3398 | F0F1 ATP synthase alpha | Cytoplasmic | 954 |
| BPSL0074 | Succinylorithine transaminase | Cytoplasmic | 700 |
| BPSL3228 | Elongation factor Tu | Cytoplasmic | 619 |
| BPSL1745 | Carbamate kinase | Cytoplasmic | 612 |
| BPSL1743 | Arginine deiminase | Cytoplasmic | 594 |
| BPSL3187 | DNA-directed RNA polymerase subunit alpha | Cytoplasmic | 549 |
| BPSL2158 | Elongation factor Ts | Cytoplasmic/ periplasmic | 547 |
| BPSL2748 | Putative oxidoreductase | Cytoplasmic | 473 |
| BPSL0892 | Putative aldo/keto reductase family oxidoreductase | Cytoplasmic | 470 |
| BPSL1510 | Nucleoside diphosphate kinase | Cytoplasmic | 460 |
| BPSL2648 | Putative protein-L-isoaspartate O-methyltransferase | Cytoplasmic | 375 |
| BPSS2288 | HSP20/alpha crystalline family protein | Cytoplasmic | 322 |
| BURPS1710b__0188 | ParA family protein | Cyto/periplasmic | 253 |
| BURPS1710b__A1046 | Alcohol dehydrogenase, zinc containing | Cytoplasmic | 197 |
| BPSL0798 | Fructose-1,6-bisphosphate aldolase | Cytoplasmic | 188 |

[a]Mowse score (33)

Further studies were performed to determine the ability to detect some of the identified proteins in a urine sample from a subject afflicted with melioidosis. Filtered urine samples from melioidosis patients were probed to detect CPS (FIGS. 12 and 15), flagellin (FIG. 13) or GroEL (FIG. 14). Control urine (−) from a healthy donor was also included in the studies. CPS was detected in 3 out of 5 patient samples (FIG. 12), flagellin in possibly 4 out of 6 patient samples (FIG. 13) and GroEL in 11 out of 11 samples (FIG. 14).

These studies support the use of the protein antigens identified by InMAD and surface polysaccharides (including CPS and LPS) for diagnosing melioidosis. In particular, these results suggest that CPS, LPS, flagellin and GroEL are indicators of melioidosis.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of diagnosing a subject with melioidosis, comprising:
 detecting, with an antibody produced by immunizing an animal with a melioidosis-associated antigen, by laboratory immunoassay, the melioidosis-associated antigen in a sample obtained from a subject exhibiting one or more signs or symptoms associated with melioidosis or a subject known to be at risk of acquiring melioidosis so as to obtain laboratory assay results regarding the presence of the melioidosis-associated antigen in the sample, wherein the melioidosis-associated antigen is a capsular polysaccharide (CPS) comprising an unbranched homopolymer of 6-deoxy-D-manno-heptose; and
 providing laboratory assay results thereby diagnosing whether the subject has melioidosis.

2. The method of claim 1, further comprising comparing detection of the melioidosis-associated antigen in the sample obtained from the subject exhibiting one or more signs or symptoms associated with melioidosis to a control, wherein increased detection of the melioidosis-associated antigen relative to a control indicates that the subject has melioidosis.

3. The method of claim 2, wherein the method is used for diagnosing a subject with acute melioidosis.

4. The method of claim 2, wherein detecting at least one melioidosis-associated antigen comprises using a lateral flow device.

5. The method of claim 1, wherein the method is used for detecting any condition or disease associated with *B. mallei, B. pseudomallei, B. thailandensis* or a combination thereof.

6. The method of claim 1, wherein the sample is a urine sample.

7. A method of monitoring the efficacy of a melioidosis therapy, comprising:
 detecting, with an antibody produced by immunizing an animal with a melioidosis-associated antigen, by laboratory immunoassay, the melioidosis-associated antigen in a sample obtained from a subject that has been administered a melioidosis therapy, wherein the melioidosis-associated antigen is a capsular polysaccharide (CPS) comprising an unbranched homopolymer of 6-deoxy-D-manno-heptose;
 comparing detection of the melioidosis-associated antigen in the sample obtained from the subject to a reference sample;
 providing laboratory assay results thereby monitoring the efficacy of the melioidosis therapy.

8. The method of claim 7, wherein the method is used for monitoring any condition or disease associated with *B. mallei, B. pseudomallei, B. thailandensis* or a combination thereof.

9. The method of claim 7, wherein the reference sample is a sample from a subject with melioidosis.

10. The method of claim 7, wherein the reference sample is a sample from a subject that does not have melioidosis.

11. The method of claim 1, wherein the antibody is produced by a hybridoma created from the immunized animal.

12. The method of claim 7, wherein the antibody is produced by a hybridoma created from the immunized animal.

13. The method of claim 1, wherein detecting comprises detecting a plurality of melioidosis-associated antigens.

14. The method of claim 7, wherein detecting comprises detecting a plurality of melioidosis-associated antigens.

15. The method of claim 1, wherein the antibody is a monoclonal antibody.

16. The method of claim 7, wherein the antibody is a monoclonal antibody.

* * * * *